United States Patent
Gao et al.

(10) Patent No.: US 9,920,363 B2
(45) Date of Patent: Mar. 20, 2018

(54) CONSTRUCTING METHOD OF HIGH-THROUGHPUT SEQUENCING LIBRARY AND USE THEREOF

(71) Applicant: BGI TECH SOLUTIONS CO., LTD., Shenzhen (CN)

(72) Inventors: Fei Gao, Shenzhen (CN); Junwen Wang, Shenzhen (CN); Tong Wang, Shenzhen (CN); Hui Jiang, Shenzhen (CN); Jinghua Wu, Shenzhen (CN); Honglong Wu, Shenzhen (CN)

(73) Assignee: BGI TECH SOLUTIONS CO., LTD., Shenzhen, Guangdong (CN)

( * ) Notice: Subject to any disclaimer, the term of this patent is extended or adjusted under 35 U.S.C. 154(b) by 142 days.

(21) Appl. No.: 14/358,674

(22) PCT Filed: Nov. 15, 2012

(86) PCT No.: PCT/CN2012/084691
§ 371 (c)(1),
(2) Date: May 15, 2014

(87) PCT Pub. No.: WO2013/071876
PCT Pub. Date: May 23, 2013

(65) Prior Publication Data
US 2014/0329697 A1    Nov. 6, 2014

(30) Foreign Application Priority Data
Nov. 15, 2011    (CN) .......................... 2011 1 0362032

(51) Int. Cl.
*C12Q 1/68*    (2006.01)
*C12N 15/10*    (2006.01)
(Continued)

(52) U.S. Cl.
CPC ....... *C12Q 1/6869* (2013.01); *C12N 15/1093* (2013.01); *C12Q 1/6806* (2013.01);
(Continued)

(58) Field of Classification Search
None
See application file for complete search history.

(56) References Cited

U.S. PATENT DOCUMENTS

2013/0295569 A1* 11/2013 Evans .................. C12Q 1/6881
435/6.11

FOREIGN PATENT DOCUMENTS

| CN | 101802223 A | 8/2010 | |
| WO | WO 2010074924 A1 * | 7/2010 | ........... C12Q 1/6809 |
| WO | WO 08/096146 A1 | 8/2010 | |

OTHER PUBLICATIONS

Heisler et al (2205) "CpG Island microarray probe sequences derived from a physical library are representative of CpG Islands annotated on the human genome." Nucleic Acids Res. 33(9):2952-61.*

(Continued)

*Primary Examiner* — Karen S. Weiler
(74) *Attorney, Agent, or Firm* — Panitch Schwarze Belisario & Nadel LLP

(57) ABSTRACT

The present invention provides a method for constructing a high-throughput sequencing library, which comprises: fragmenting genomic DNA; end-repairing the DNA fragments; adding a base A to the 3' end of the end-repaired DNA fragments; connecting the DNA fragments having cohesive end A with a methylated adapter; carrying out hybrid capture on the connection products by using specific probes to obtain object fragments; treating the object fragments with bisulfite, to convert non-methylated cytosines to uracils; PCR amplifying the converted object fragments; and separating and purifying the amplification products, wherein the (Continued)

amplification products constitute the high-throughput sequencing library. The present invention also provides a method and an apparatus for identifying methylation information in specified genome regions of a sample.

12 Claims, 6 Drawing Sheets

(51) Int. Cl.
C40B 40/06 (2006.01)
C40B 40/08 (2006.01)
C40B 50/06 (2006.01)

(52) U.S. Cl.
CPC ............ C12Q 1/6876 (2013.01); C40B 40/06 (2013.01); C40B 40/08 (2013.01); C40B 50/06 (2013.01)

(56) References Cited

OTHER PUBLICATIONS

Lee et al (2011) "Targeted bisulfite sequencing by solution hybrid selection and massively parallel sequencing" Nucleic Acids Research 39(19):e127.*
Li et al. (2010) "The DNA Methylome of Human Peripheral Blood Mononuclear Cells" PLoS Biology 8(11):e1000533.*
Kenny et al (2011) "Multiplex Target Enrichment Using DNA Indexing for Ultra-High Throughput SNP Detection" DNA Research 18:31-38.*
Butkus et al. (1987) "Synthesis and physical characterization of DNA fragments containing N4-methylcytosine and 5-methylcytosine." Nucleic Acids Research 15(20):8467-8478.*
Duncavage et al (2011) "Hybrid Capture and Next-Generation Sequencing Identify Viral Integration Sites from Formalin-Fixed, Paraffin-Embedded Tissue" J Mol Diagn. 13(3): 325-333.*
Ball et al. (2009) "Targeted and genome-scale strategies reveal gene-body methylation signatures in human cells" Nature Biotechnology 27(4):361-368.*
Ravi et al. (2011) "The Agilent Technologies' SureSelect™ All Exon Product Portfolio: High Performance Target Enrichment System for Human and Mouse Exome Sequencing on Illumina and SOLiD Platforms" Journal of Biomolecular Techniques 22(Supp):S41.*
Clark et al. (2011) "Performance comparison of exome DNA sequencing technologies" Nature Biotechnology 29(10):908-914.*
Strachan et al. (2010) Table 9.5 Human Genome and Human Gene Statistics, In: Human Molecular Genetics, 4th ed., Garland Science, p. 267.*
WIPO Application No. PCT CN 12/084691, PCT International Search Report and Written Opinion of the International Searching Authority dated Feb. 14, 2013.
WIPO Application No. PCT CN 12/084691, PCT international Preliminary Report on Patentability, dated May 20, 2014.
Teer et al., "Systematic comparison of three genomic enrichment methods for massively parallel DNA sequencing," Genome Research, vol. 20, pp. 1420-1431 (2010).

* cited by examiner (a)

Promoter
(b)

(c)

CONSTRUCTING METHOD OF HIGH-THROUGHPUT SEQUENCING LIBRARY AND USE THEREOF

CROSS-REFERENCE TO RELATED APPLICATION

This application is a US national stage of PCT/CN2012/084691 filed Nov. 15, 2012, which claims priority to Chinese Patent Application No. 201110362032.2 filed in the State Intellectual Property Office (SIPO) of PR China on Nov. 15, 2011, the entire content of which is incorporated herein by reference.

REFERENCE TO A SEQUENCE LISTING

This application incorporates by reference the Sequence Listing submitted in Computer Readable Form as file 446367SEQLST.TXT, created on Feb. 3, 2016, and containing 6,400 bytes.

FIELD OF THE INVENTION

The present invention relates to biotechnical field. Specifically, it relates to DNA methylation detection technology, and particularly relates to the detection of methylation in specified genomic regions. More specifically, the present invention provides a method for constructing a high-throughput sequencing library, a method for identifying methylation information in specified genomic regions of a sample, an apparatus for determining methylation information in specified genomic regions of a sample; and a kit for constructing a high-throughput sequencing library of specified genomic regions of a sample.

BACKGROUND OF THE INVENTION

DNA methylation is one of the most deeply-studied epigenetic mechanisms, DNA methylation plays an important role in the maintenance of normal function of cell, protection of the genomic integrity from the damage of parasitic DNA fragments, chromatin structure modification, X-chromosome inactivation, genomic imprinting, embryonic development and human tumorigenesis, and DNA methylation has become one of the most active research fields at present.

However, at present, methods for the detection of methylation in specified genomic regions, such as promoter regions, CpG island regions, CGI shore regions and imprinted gene regions, are still to be improved.

SUMMARY OF THE INVENTION

The aim of the present invention is to solve at least one of the problems in prior art. Therefore, the present invention provides a method for constructing a high-throughput sequencing library and use thereof, so as to test typically the methylation information in specified genomic regions.

According to one aspect of the present invention, the present invention provides a method for constructing a high-throughput sequencing library. According to one example of the present invention, the method comprises the following steps: fragmentsing genomic DNA to obtain DNA fragments; end-repairing the DNA fragments to obtain end-repaired DNA fragments; adding a base A to the 3' end of the end-repaired DNA fragments to obtain DNA fragments having cohesive end A; connecting the DNA fragments having cohesive end A with a methylated adapter to obtain connection products; carrying out hybrid capture on the connection products by using specific probes to obtain object fragments; PCR amplifying the object fragments to obtain amplification product; and separating and purifying the amplification product, wherein the separated and purified amplification product constitutes the high-throughput sequencing library. According to one example of the present invention, the specific probes to be used are specific for known methylation sites, for example, the specific probes are designed based on using human genome as a reference sequence and using genomic regions known to have methylation sites as target sequences, wherein the genomic regions known to have methylation sites may be a coding region or promoter region of at least one of the genes listed in Table I below.

TABLE I-1

| | | Molecular function-related genes |
|---|---|---|
| Molecular function | GO ID (GO Number) | Gene names |
| Histone | GO: 0004402 | CDY1B ARRB1 ELP3 KAT2A SAP130 NCOA3 CREBBP KAT8 METTL8 TADA3 TADA2A TAF6L MGEA5 KAT6B TAF9 KAT5 NCOA1 SUPT3H TAF5 SRCAP HAT1 CDY2B EPC1 KAT6A CLOCK EP300 TAF12 TAF1 GTF3C4 MED24 KAT2B CDYL TAF5L ING3 PET117 BRCA2 ELP4 EDF1 BAZ1A SUPT7L TAF10 NCOA2 KAT7 TAF1L TADA1 |
| | GO: 0004407 | SALL1 HDAC11 HDAC1 HDAC8 HDAC2 HDAC10 HDAC5 HDAC3 HDAC4 HDAC6 MTA2 MTA2 SIRT1 HDAC9 |
| | GO: 0008469 | PRMT5 PRMT8 PRMT2 PRMT7 |
| | GO: 0010484 | KAT2A BRCA2 |
| | GO: 0010485 | BRCA2 USP22 |
| | GO: 0017136 | SIRT6 SIRT2 SIRT1 |
| | GO: 0018024 | EZH2 EHMT2 SETD7 SUV39H2 ASH1L MEN1 SETD8 EHMT1 DOT1L SUV39H1 PRDM2 SMYD3 SETDB1 SETMAR SUV420H1 PRDM9 PRDM6 MLL2 WHSC1 WHSC1L1 SETD1A SETD2 |
| | GO: 0031493 | L3MBTL1 |
| | GO: 0032041 | HDAC7 HDAC11 HDAC1 HDAC8 HDAC2 HDAC10 HDAC5 HDAC3 HDAC4 HDAC6 HDAC9 |
| | GO: 0032452 | KDM2B PHF8 KDM1A PHF2 JARID2 |
| | GO: 0032453 | C14orf169 KDM1A |
| | GO: 0032454 | KDM4C PHF8 JHDM1D KDM1A PHF2 |

TABLE I-1-continued

Molecular function-related genes

| Molecular function | GO ID (GO Number) | Gene names |
|---|---|---|
| | GO: 0033746 | JMJD6 |
| | GO: 0033749 | JMJD6 |
| | GO: 0034647 | KDM5B |
| | GO: 0034648 | KDM5B KDM1B KDM1A |
| | GO: 0034649 | KDM1B |
| | GO: 0034739 | HDAC7 HDAC11 HDAC1 HDAC8 HDAC2 HDAC10 HDAC5 HDAC3 HDAC4 HDAC6 HDAC9 |
| | GO: 0035033 | NCOR1 MAPK8 TP53 |
| | GO: 0035034 | EID1 |
| | GO: 0035035 | EGR1 SP1 SIRT2 TRIM68 ZBTB7A EID1 TP53 MEF2A FOXP3 EPAS1 GLI3 HIF1A TAF7 |
| | GO: 0035064 | CHD8 CHD1 CBX2 ING4 KAT8 SUZ12 ING1 L3MBTL2 LRWD1 PHF13 CBX5 NCAPD3 PHF8 ING2 CCDC101 RAG2 CBX4 WDR92 GLYR1 JHDM1D CBX8 SPIN1 RBBP5 ING3 ING5 TRIM24 TDRD3 MSL3 UHRF1 CBX7 PHF2 L3MBTL1 NCAPG2 RRP8 |
| | GO: 0035173 | BAZ1B CDK1 CCNB1 CDK2 |
| | GO: 0035174 | ATM PRKAA1 PRKAA2 |
| | GO: 0035401 | JAK2 |
| | GO: 0035402 | CHEK1 PKN1 |
| | GO: 0035403 | PRKCA PRKCB |
| | GO: 0035575 | PHF8 JHDM1D |
| | GO: 0035642 | CARM1 |
| | GO: 0042054 | EZH2 PRMT1 SUZ12 PRMT6 CARM1 EED SUV39H1 PRMT2 NSD1 |
| | GO: 0042393 | CHD8 IPO9 UIMC1 SNCA ASF1A RSF1 LEF1 CHAF1B RCC1 BRD7 DTX3L PRMT6 DNAJC2 TONSL L3MBTL2 USP16 SMARCA5 NPM2 H2AFX TBL1X IPO7 RNF8 COPR5 ASF1B HILS1 RBBP4 RNF168 CTSL1 HJURP USP3 RAG1 JAK2 TBL1XR1 DEK APBB1 NCAPD2 NASP HINFP UHRF2 RNF20 PRKCB SET CTCFL MYSM1 MCM2 PKN1 UHRF1 AIRE NPM1 SIRT1 L3MBTL1 CD1D PRMT7 |
| | GO: 0042799 | SUV420H2 SUV420H1 NSD1 |
| | GO: 0042800 | CXXC1 MLL4 MLL3 MLL PRDM7 ASH2L WDR5 SETD1B RBBP5 WDR82 MLL5 SETD1A MLL3 |
| | GO: 0042826 | TRAF6 TAL1 NCOR1 HDAC1 KAT2A SP1 KPNA2 NIPBL SIRT2 MAPK8 NR2C1 PHB RAD9A HR GMNN HES1 NCOR2 HDAC10 YWHAB UHRF1BP1 SUDS3 CBX5 SP2 LPIN1 MEF2D ANKRA2 MEF2A RBBP4 ANKRD1 FOXP3 HDAC3 NKX3-1 MEF2C HDAC4 TOP2B NUDT21 KAT2B YWHAE GLI3 BCOR RFXANK HDAC6 TCF21 MEF2B CAMTA2 PKN2 TOP2A HIF1A PKN1 PRDM1 TFAP4 NRIP1 HDAC9 USF1 HEY2 |
| | GO: 0043997 | KAT2A |
| | GO: 0044020 | PRMT1 PRMT6 PRMT7 |
| | GO: 0046811 | SKI |
| | GO: 0046969 | SIRT6 HDAC7 HDAC11 HDAC1 HDAC8 HDAC2 HDAC10 HDAC5 HDAC3 HDAC4 HDAC6 SIRT1 HDAC9 |
| | GO: 0046970 | HDAC7 HDAC11 HDAC1 HDAC8 HDAC2 HDAC10 HDAC5 HDAC3 HDAC4 HDAC6 HDAC9 |
| | GO: 0046974 | EHMT2 SUV39H2 SETDB2 EHMT1 SUV39H1 |
| | GO: 0046975 | SETD3 NSD1 SMYD2 |
| | GO: 0046976 | EHMT2 EZH1 EHMT1 |
| | GO: 0051864 | KDM2B PHF8 JMJD5 JHDM1D NO66 KDM2A KDM4A |
| | GO: 0070577 | BAZ2A BRD7 CARM1 MLL BAZ1B SMARCA4 TAF1 TRIM24 |
| | GO: 0070611 | PRMT6 |
| | GO: 0070612 | PRMT6 |
| | GO: 0071207 | SLBP ERI1 |
| | GO: 0071208 | SNRPD3 LSM10 SLBP |
| | GO: 0071558 | PHF8 JHDM1D |
| | GO: 0072354 | GSG2 |
| Chromatin | GO: 0003682 | SALL1 ZEB1 HDAC7 POLG GATA1 MBD2 CBX2 PRMT5 KLHDC3 TIGD4 TAL1 ASF1A SHMT2 SMC1A LEF1 SATB2 C15orf42 VCX KAT2A PATZ1 CHAF1B CUX1 JUB WAC PROP1 MBD5 KDM5A SUV39H2 DNMT3A RCC1 PHC1 ATF2 SUZ12 TWIST2 MEOX1 CITED1 NR3C1 MEN1 TLE1 DNAJC2 HDAC2 APITD1 TOP1 EED ISL1 NCOR2 HCFC1 NCOA6 UPF1 CITED2 CHD7 BAHD1 CENPB POLD1 POU4F2 SMARCC1 HIRA TP73 MPO FOXP4 EZH1 SF3B1 HELLS LRWD1 MLH3 PHF13 MBD3 CBX5 DLX1 SMARCE1 MITF DLX2 NKX6-1 MKRN9P BCL6 SREBF2 SMAD2 PHF8 GLI2 TP53 RNF8 MKRN1 MCMBP MLL REST DHX30 RNF168 RAN ING2 HMGN5 CRX SUV39H1 MBD6 TSHZ3 FOXP1 RAG2 SIN3B TP63 BAZ1B FOXP3 HDAC3 SOX15 CBX4 FANCM SMARCA4 POLE ADNP TLE4 NKX2-2 SMAD6 ATRX YBX2 |

TABLE I-1-continued

Molecular function-related genes

| Molecular function | GO ID (GO Number) | Gene names |
|---|---|---|
| | | APBB1 CHD6 PRKAA1 RNF2 NR5A1 POLA1 CENPA PHC1B RBMX NUP62 H2AFY GATA6 BARX2 SOX10 CBX1 NKAP PSIP1 ESR1 JMJD5 CDCA5 TCF7L1 HHEX HOXD1 DDX1 SP3 HINFP TOP2B SREBF1 PBX2 PBRM1 ATXN7 GLI3 FABP1 PAX3 YAP1 PRKCB WHSC1 TOX3 PARG SOX9 HMGN5 TRIM24 FOXP2 TDRD3 CAMTA2 GATA2 BMI1 SKIL HMGN3 KDM1A EGR2 NEUROD1 PCGF2 SMAD4 PRKAA2 MED1 TOP2A TTF1 RELA PKN1 ERCC6 NEUROG1 TCF7L2 TCF7 SSBP1 CENPF NKX2-5 RING1 MSH6 AIRE HESX1 C19orf40 CDC6 HOXD13 CHAF1A NSD1 CTNNB1 APTX NFATC3 TFAM PDX1 TFAP2A TGIF1 MNT NCOA2 ZKSCAN3 L3MBTL1 HES5 ACTL6A SIN3A JARID2 BAP1 RFX4 GMNC PHF21A |
| | GO: 0031490 | SMAD3 FOXS1 RARA TOP1 BCL6 APEX1 FOXC2 EP300 VAX2 ATOH1 ZIC2 TOP1MT VAX1 NOTCH1 FOXC1 |
| | GO: 0043035 | CTCF |

TABLE I-2

Biological processing-related genes

| Biological processing | GO_ID (GO Number) | Gene name |
|---|---|---|
| DNA methylation | GO: 0006306 | EHMT2 DNMT3L FOS BAZ2A HEMK1 DNMT3A DMAP1 DNMT3B EHMT1 MLL DKFZp686N1286 ATRX GNAS ATF7IP GATAD2A MGMT TRDMT1 MLL5 DNMT1 |
| | GO: 0010216 | HELLS CTCF DNMT1 |
| | GO: 0010424 | DNMT3A DNMT3B SMARCA4 |
| | GO: 0043045 | DNMT3A PICK1 DNMT3B ZFP57 |
| | GO: 0043046 | TDRD9 TDRD5 DNMT3A PICK1 PIWIL4 TDRD1 AOF1 PLD6 MAEL ASZ1 PIWIL2 CTCFL PRMT7 |
| | GO: 0044030 | AOF1 KDM1B |
| | GO: 0060821 | SMCHD1 |
| Histone modification | GO: 0000415 | BCOR |
| | GO: 0000416 | PAXIP1 |
| | GO: 0010390 | WAC DTX3L RNF40 RAG1 CDC73 PAF1 RNF20 CTR9 LEO1 UBE2E1 |
| | GO: 0010452 | SETD3 NSD1 SETD2 SMYD2 |
| | GO: 0016570 | AURKC HLCS RTF1 AURKB |
| | GO: 0016571 | EZH2 PRMT8 PRMT1 SUZ12 PRMT6 CARM1 EED SUV420H2 MLL3 EHMT1 SUV39H1 PRDM7 SUV420H1 WHSC1L1 CTCFL PRMT2 NSD1 SATB1 MLL3 PRMT7 |
| | GO: 0016572 | RPS6KA4 RPS6KA5 BAZ1B MAP3K12 CDK2 |
| | GO: 0016573 | NCOA3 CREBBP KAT8 KAT6B CPA4 CSRP2BP KAT5 MBD3 TAF5 SRCAP HAT1 KAT6A EP300 TAF1 GTF3C4 TRRAP PET117 BMI1 ELP4 PCGF2 TAF1L |
| | GO: 0016574 | HUWE1 SUZ12 UBE2N RNF2 CBX8 BMI1 USP22 RING1 |
| | GO: 0016575 | SALL1 HDAC11 HDAC1 BAZ2A SIRT2 HDAC8 PHB MORF4L1 HDAC2 HDAC10 RBM14 HDAC5 HDAC3 PRDM5 HDAC4 HDAC6 HOPX SIRT1 HDAC9 |
| | GO: 0016576 | EYA1 EYA2 EYA3 |
| | GO: 0016577 | KDM2B KDM6B KDM4A KDM1A |
| | GO: 0016578 | ATXN7L3 KAT2A ENY2 USP16 SUPT3H USP3 USP21 ATXN7 TRRAP MYSM1 USP22 TAF10 |
| | GO: 0031056 | CDK9 UBE2B |
| | GO: 0031058 | UBE2N |
| | GO: 0031060 | CTCF |
| | GO: 0031061 | JARID2 |
| | GO: 0031062 | MEN1 |
| | GO: 0031063 | MAPK8 |
| | GO: 0031064 | SKI FOXP3 |
| | GO: 0031065 | NCOR1 NIPBL PML TP53 LPIN1 CTBP1 SREBF1 TGFB1 |
| | GO: 0033128 | TWIST1 UBE2B |
| | GO: 0033129 | RPS6KA4 IL1B RPS6KA5 MAPK3 CCNB1 |
| | GO: 0033169 | KDM4C PHF8 JHDM1D HSF4 KDM3A KDM1A PHF2 |

TABLE I-2-continued

Biological processing-related genes

| Biological processing | GO_ID (GO Number) | Gene name |
|---|---|---|
| | GO: 0033182 | UBE2N |
| | GO: 0033522 | UBE2A RNF8 UBE2B UBR2 |
| | GO: 0033523 | RNF8 RNF40 CDC73 PAF1 RNF20 CTR9 LEO1 UBE2E1 |
| | GO: 0034720 | AOF1 KDM5B KDM1B C14orf169 KDM1A |
| | GO: 0034721 | KDM5B |
| | GO: 0034770 | NSD1 |
| | GO: 0034968 | SETD7 MEN1 SETD8 EHMT1 DOT1L SUV39H1 SMYD3 SUV420H1 WDR92 WHSC1L1 |
| | GO: 0034969 | PRMT8 PRMT2 PRMT7 |
| | GO: 0034970 | PRMT6 CARM1 |
| | GO: 0034971 | CARM1 |
| | GO: 0035065 | MYOCD EID1 GATA2 CTCF |
| | GO: 0035066 | PPARGC1A ARRB1 BRD7 RPS6KA4 IL1B RPS6KA5 BRCA1 FOXP3 NOS1 PAXIP1 MAPK3 TGFB1 |
| | GO: 0035067 | SNCA CTBP1 FOXP3 TWIST1 SET TAF7 |
| | GO: 0035404 | PRKAA1 PRKAA2 |
| | GO: 0035407 | CHEK1 PKN1 |
| | GO: 0035408 | PRKCA PRKCB |
| | GO: 0035409 | JAK2 |
| | GO: 0035518 | KDM2B SKP1 RYBP RNF2 PCGF1 BCOR RING1 |
| | GO: 0035522 | BAP1 |
| | GO: 0035574 | PHF8 JHDM1D |
| | GO: 0035978 | HMGA2 |
| | GO: 0043966 | LEF1 KAT2A SAP130 ING4 POLE3 PHF16 SPI1 TADA3 TADA2A TAF6L BRPF3 KAT6B TAF9 CSRP2BP SUPT3H MBIP POLE4 YEATS2 KAT6A PHF17 CCDC101 TAF12 TRIM16 SMARCA4 IRF4 WDR5 BRPF1 MAP3K7 KAT2B TAF5L TCF3 ING5 BRCA2 BRD1 SUPT7L TAF10 PHF15 KAT7 TADA1 DR1 |
| | GO: 0043967 | RUVBL2 LEF1 ARRB1 MORF4L1 RUVBL1 DMAP1 EPC1 EP300 TRIM16 APBB1 IRF4 TRRAP TCF3 ING3 BRCA2 USP22 YEATS4 EP400 BRD8 ACTL6A |
| | GO: 0043968 | RUVBL2 MEAF6 MORF4L1 RUVBL1 DMAP1 EPC1 TRRAP ING3 YEATS4 EP400 BRD8 ACTL6A |
| | GO: 0043973 | LDB1 |
| | GO: 0043981 | ING4 MEAF6 PHF16 PHF17 PHF15 KAT7 |
| | GO: 0043982 | ING4 MEAF6 PHF16 PHF17 PHF15 KAT7 |
| | GO: 0043983 | ING4 MEAF6 PHF16 PHF17 BRD4 PHF15 KAT7 |
| | GO: 0043984 | ING4 MEAF6 PHF16 KAT8 MSL1 MLL PHF17 MSL3 PHF15 KAT7 MSL2 |
| | GO: 0043985 | PRMT5 PRMT1 PRMT6 COPR5 PRMT7 |
| | GO: 0043987 | RPS6KA4 RPS6KA5 |
| | GO: 0043988 | RPS6KA4 RPS6KA5 |
| | GO: 0043990 | RPS6KA5 |
| | GO: 0044154 | KAT2A MEAF6 BRD4 |
| | GO: 0051567 | EHMT2 SUV39H2 SETDB2 EHMT1 SUV39H1 PRDM5 |
| | GO: 0051568 | CXXC1 MLL4 DPY30 MLL KDM6A ASH2L WDR5 SETD1B MLL2 PAXIP1 RBBP5 WDR82 MLL5 SETD1A |
| | GO: 0051569 | MLL CTCFL |
| | GO: 0051571 | DNMT3B BRCA1 MYB PAXIP1 OGT DNMT1 |
| | GO: 0051572 | GFI1B BCOR |
| | GO: 0051573 | DNMT3B BRCA1 PAX5 DNMT1 |
| | GO: 0051574 | GFI1B MYB JARID2 |
| | GO: 0070076 | UBE2B |
| | GO: 0070078 | JMJD6 |
| | GO: 0070079 | JMJD6 |
| | GO: 0070512 | BRCA1 |
| | GO: 0070535 | RNF168 |
| | GO: 0070537 | UIMC1 BRCC3 |
| | GO: 0070544 | PHF8 JMJD5 JHDM1D NO66 KDM4A |
| | GO: 0070734 | EHMT2 EHMT1 |
| | GO: 0070932 | HDAC1 HDAC4 SIRT1 HDAC9 |
| | GO: 0070933 | HDAC1 RCOR1 REST HDAC4 HDAC9 |
| | GO: 0071110 | HLCS |
| | GO: 0071557 | PHF8 JHDM1D |
| | GO: 0071894 | WAC |
| | GO: 0072355 | GSG2 |
| | GO: 0090241 | SPI1 CTBP1 |
| | GO: 2000615 | CHEK1 |

TABLE I-2-continued

| Biological processing | GO_ID (GO Number) | Gene name |
|---|---|---|
| | GO: 2000617 | BRCA1 |
| | GO: 2000620 | BRCA1 |
| Epigenetics | GO: 0040029 | GPX1 BAZ1B GLMN CTCF |
| | GO: 0040030 | ASIP CTCF |
| | GO: 0045814 | SPI1 TRIM27 DNMT3B EPC1 CREBZF |
| | GO: 0045815 | SLC50A1 |
| Gene imprinting | GO: 0006349 | DIRAS3 DNMT3L DNMT3A GSK3A EED KDM1B DNMT3B KDM1B ZFP57 CTCFL KCNQ1 CTCF IGF2 PRMT7 |
| | GO: 0071514 | ASIP NDN GNAS AXIN1 |
| Chromatin status | GO: 0000183 | BAZ2A SIRT2 SMARCA5 SUV39H1 SIRT1 RRP8 |
| | GO: 0001672 | TLK1 TLK2 |
| | GO: 0006325 | SAFB EZH2 VCX HMGB2 SOX2 LRWD1 HMG20B HDAC5 HMGA2 SUV39H1 SOX15 SOX1 HIST1H4K TCF7L1 HMGN2 HMG20A MUM1 ACTL6B SATB1 |
| | GO: 0006333 | ASF1A SUV39H2 HDAC8 SMARCA5 ASF1B BAZ1B CHD3 HIRIP3 MTA2 |
| | GO: 0006338 | CHD1 HDAC1 RSF1 ARID1A SMARCC2 SMARCD1 SATB2 KAT2A BAZ2A SUV39H2 CHD1L RERE INO80 SMARCB1 TAF6L MEN1 BPTF FOXA1 HDAC2 SUPT6H SMYD1 SMARCC1 SUPT5H SMARCA5 NPM2 SMARCE1 HDAC5 HILS1 RBBP4 SMARCA2 SMARCD3 FOXP3 SMARCA4 MYB CHD6 HNF1A SMARCA1 HDAC4 KAT2B PBRM1 BNIP3 ACTL6B SUPT4H1 CHRAC1 SOX9 CBX3 TTF1 BAZ1A RB1 TNP1 ACTL6A KLF1 SMARCD2 |
| | GO: 0006342 | SIRT2 HDAC5 HILS1 SIRT4 MLL2 SIRT5 UBR2 SIRT1 TNP1 |
| | GO: 0006343 | SIRT1 |
| | GO: 0006344 | HDAC2 UBE2B SIRT1 |
| | GO: 0006346 | DNMT3A HELLS MBD3 DNMT3B SMARCA4 SIRT1 |
| | GO: 0006348 | SIRT2 HAT1 |
| | GO: 0016568 | CHD8 UTY CHD9 HDAC7 UIMC1 RUVBL2 CBX2 PRMT5 EPC2 ATXN7L3 RBBP7 NCOR1 HDAC11 BRE HDAC1 KDM2B ASF1A KDM4D EZH2 EHMT2 EYA1 RBL2 MSL3P1 UTP3 ING4 MEAF6 SETD7 MLL4 WAC KDM5A PHF1 CBX6 ASH1L DNMT3A KAT8 ARID2 HDAC8 SUZ12 VPS72 ASXL1 MORF4L1 C20orf20 DTX3L NR3C1 PRMT6 CARM1 ENY2 DNAJC2 HDAC2 BANP BAP18 BRPF3 EYA4 SS18L1 KAT6B DPY30 MSL1 EED TLK1 KAT5 SETD3 CHD7 CABIN1 BAHD1 UBE2A HDAC10 L3MBTL2 USP16 HIRA AEBP2 TSPYL2 RUVBL1 FOXA3 SUV420H2 EZH1 BCORL1 KDM4C SETDB2 LRWD1 DMAP1 PHF13 SUDS3 C11orf30 TAF5 SETD8 MLL3 BRCC3 H2AFY2 SRCAP KDM5B RCOR1 EHMT1 PHF8 HAT1 KDM1B RNF8 COPR5 RCBTB1 HLTF HMG20B MLL HDAC5 ASF1B GFI1B MORF4L2 RNF168 EPC1 KAT6A DOT1L KDM3B ING2 HMGN5 JMJD6 SUV39H1 CCDC101 RNF40 RAG2 SMARCAL1 PRDM7 USP3 SMYD3 SETDB1 RAG1 SETMAR KDM6A KDM4B SUV420H1 FAM175A HDAC3 JAK2 ARID1B UBN1 CBX4 PADI4 TBL1XR1 MBTD1 ASH2L PRDM5 TET1 SMARCAD1 TLK2 DEK PRDM9 APBB1 CHD3 PRKAA1 USP21 WDR5 H2AFY CECR2 DAPK3 PRDM6 JMJD5 HDAC4 BRPF1 HMG20A SETD1B MLL2 EYA2 KDM5C RNF20 JHDM1D CBX8 BCOR NO66 TRRAP RBBP5 L3MBTL3 KDM3A HDAC6 ING3 PRKCB WHSC1 WHSC1L1 ING5 KDM2A KDM6B CTCFL KDM4A MYSM1 TDRD3 BMI1 MSL3 HMGN3 KDM1A BRD1 KDM4DL PRKAA2 CHD4 PKN1 CHD5 USP22 RBL1 YEATS4 RING1 GSG2 FOXA2 EP400 BRD8 NSD1 L3MBTL4 EYA3 CBX7 PHF2 MLL5 SETD1A KAT7 SATB1 L3MBTL1 SETD2 IKZF1 HDAC9 BABAM1 CTCF SMYD2 BAG6 DPF3 RRP8 DNMT1 JARID2 BAP1 JMJD1C KDM5D PRMT7 PHF21A |
| | GO: 0031497 | CHAF1B RBBP4 C2orf65 CHAF1A |
| | GO: 0031507 | BAHD1 HMGA2 |
| | GO: 0031508 | CENPV HELLS |

TABLE I-2-continued

| Biological processing | GO_ID (GO Number) | Gene name |
|---|---|---|
| | GO: 0031936 | ASF1A HMGA1 |
| | GO: 0031937 | SIRT1 |
| | GO: 0034401 | CTBP1 |
| | GO: 0034509 | HJURP |
| | GO: 0035092 | TSSK6 H1FNT SEP15 |
| | GO: 0035986 | HMGA1 CDKN2A HMGA2 |
| | GO: 0043044 | CHD8 SMARCA5 BAZ1B SMARCA1 |
| | GO: 0045799 | TAL1 |
| | GO: 0048096 | ARID1A SMARCD1 WBP7 NR3C1 BAZ1B ARID1B CHEK1 |
| | GO: 0061188 | PHF8 PHF2 |
| | GO: 0070827 | SUPV3L1 |
| | GO: 0090308 | POU5F1 |
| | GO: 0090310 | APOBEC1 AICDA TET1 |
| RNA interference | GO: 0016246 | CELF1 |
| | GO: 0030422 | TARBP2 PRKRA DICER1 |
| | GO: 0030423 | TARBP2 DICER1 CLP1 |
| | GO: 0035087 | CLP1 |
| RNA modification | GO: 0001510 | FTSJ2 HENMT1 FTSJ1 TGS1 METTL14 METTL3 FTSJ3 |
| | GO: 0002098 | MOCS3 CTU2 URM1 CTU1 |
| | GO: 0006400 | QTRT1 AARS SSB GTPBP3 WDR4 THG1L CDK5RAP1 METTL1 |
| | GO: 0009451 | CDKAL1 PARN CDK5RAP1 |
| | GO: 0016556 | ADAR APOBEC1 ADARB1 DNAJB11 AICF APOBEC2 |
| | GO: 0030488 | TRMT61B NSUN2 ALKBH8 TRMT61A |
| | GO: 0031167 | FTSJ2 |
| | GO: 0034227 | MOCS3 CTU2 URM1 CTU1 |
| | GO: 0035553 | FTO |
| | GO: 0080009 | FTSJD2 |

TABLE I-3

Cellular components-related genes

| Cellular components | GO ID (GO Number) | Gene name |
|---|---|---|
| Nucleosome | GO: 0000786 | HIST1H2AD HIST2H3A HIST1H2AJ HIST1H1D HIST1H1C HIST1H2BH HIST1H2BO HIST2H2BE HIST1H2BN HIST1H2BB H2AFJ HIST2H2BF MYST3 H2AFB3 H3F3A HIST1H2BC PRM3 KAT6B HIST3H3 HIST1H1E HP1BP3 HIST1H2AC HIST1H2AB HIST3H2BB HIST1H4A SHPRH HIST1H3G H2AFX H2AFB1 HIST2H3PS2 HIST1H2BM HIST1H2BF H3F3B HIST1H1A H2AFY2 HIST2H2AA3 H2AFV H1FOO HILS1 H3F3C KAT6A HIST1H2BJ HIST1H2AA CENPA HIST1H4K H1F0 HIST1H2AH H2AFY HIST1H2BL PRM1 HIST2H2AB HIST1H4G HIST3H2A HIST2H2BD HIST1H1B HIST1H1T H2BFS H2BFWT TNP2 HIST1H2BA H2AFZ HIST2H2AC HIST1H2BK PRM2 HIST1H2BD TNP1 HIST1H2AL H2BFM HIST2H2BC H1FX |
| | GO: 0000788 | IRF4 TCF3 |
| Histone | GO: 0000118 | HDAC7 MBD2 TAL1 NCOR1 HDAC11 HDAC1 SATB2 RERE HDAC8 HR TAF6L NCOR2 MECOM HDAC10 TBL1X CBX5 HDAC5 SAP18 HDAC3 TBL1XR1 HDAC4 ZNF217 HDAC6 MTA2 NRIP1 HDAC9 CIR1 SAP30 PHF21A |
| | GO: 0000123 | ING4 PHF16 CREBBP PHF17 EP300 PHF15 KAT7 |
| | GO: 0032777 | KAT5 EPC1 ING3 |
| | GO: 0035097 | CXXC1 MLL4 MEN1 DPY30 CBX5 MLL3 MLL KDM6A ASH2L WDR5 SETD1B MLL2 PAXIP1 RBBP5 WDR82 SETD1A MLL3 HDAC9 JARID2 |
| | GO: 0035267 | RUVBL2 MEAF6 MORF4L1 KAT5 RUVBL1 DMAP1 EPC1 TRRAP ING3 ACTB YEATS4 EP400 BRD8 ACTL6A |
| | GO: 0043189 | MRGBP |
| | GO: 0070776 | MEAF6 BRPF3 KAT6B KAT6A BRPF1 ING5 BRD1 |
| | GO: 0071204 | SYNCRIP SLBP YBX1 ERI1 LSM11 |
| Chromatin | GO: 0000785 | KLF4 KIF22 STAG2 NEDD4 TMPO ARRB1 RBL2 PPP1R10 TOX4 DSCC1 HMGN4 SUV39H2 MYCN MEN1 PDSSA HMGA1 WAPAL FANCC NFE2L2 OIP5 UPF1 SNW1 UBE2A TP73 HMGN1 SMC3 ATP1B4 MCM7 TP53 REST MAEL ASF1B PDS5B RAN HMGA2 HMGN5 JUNB TP63 EP300 HDAC3 JUND AHCTF1 HLCS MAF EIF3E CHEK1 POLA1 |

TABLE I-3-continued

Cellular components-related genes

| Cellular components | GO ID (GO Number) | Gene name |
|---|---|---|
| | | MBD4 F5H568 UBE2B CBX1 CDK4 HMGN2 TRIM28 ESCO2 CCND2 PARG HMGN5 WDR82 CAPN2 STAG1 MCM2 ID2 CBX3 HMGN3 UBR2 CENPF APTX ESCO1 RB1 SATB1 L3MBTL1 MAU2 RCOR2 SIN3A |
| | GO: 0000789 | NPM2 |
| | GO: 0000790 | KLHDC3 CREB1 TAL1 NCOR1 ARID1A PPP1R10 RCC1 LDB1 MRE11A RARA HDAC2 CEBPB RFX3 CITED2 UBE2A HIRA NPM2 KDM4C JUN AR POGZ HAND2 GATA3 TIMELESS TP53 NR1H3 MEF2A PHOX2B SMARCA2 SNAI2 SRF USP3 SMARCD3 SCRT2 HNRNPK PAX6 SMARCA4 NR1D1 MEF2C UBE2B H1FNT DDX11 TIPIN CDCA5 PHOX2A CBX8 PLCB1 BRD4 RXRA KDM1A PCGF2 STAT6 SLX4 MSH6 MYOD1 APTX CBX7 FER SIRT1 |
| | GO: 0000791 | DNMT3A |
| | GO: 0000792 | SALL1 MBD2 CBX2 CBX6 HDAC2 DAXX ORC2 MBD3 SUV39H1 SMARCA4 MECP2 TOP2B CBX8 SALL4 UHRF1 CBX7 |
| | GO: 0001739 | PHC1 SUZ12 EED RNF2 PHC1B PCGF2 RING1 |
| | GO: 0005677 | BAZ2A SIRT2 BAHD1 SMARCA5 SUV39H1 SIRT1 RRP8 |
| | GO: 0005678 | NAP1L3 CHAF1B NAP1L2 NAP1L1 CHAF1A NAP1L4 |
| | GO: 0005719 | SMARCA4 RBMX CECR2 TRIM28 TRIM24 CBX3 ALKBH1 SIRT1 |
| | GO: 0005720 | TCP1 DNMT3L SUV39H2 DNMT3A VDR CBX5 DNMT3B ATRX AICF CBX1 PSIP1 TRIM28 CBX3 SIRT1 SATB1 FOXC1 |
| | GO: 0005721 | HELLS LRWD1 BAZ1B INCENP CBX1 IKZF1 DNMT1 |
| | GO: 0005724 | SIRT6 TNKS1BP1 |
| | GO: 0005726 | NUFIP1 SMARCA4 TRIM24 |
| | GO: 0008623 | CHRAC1 BAZ1A |
| | GO: 0016585 | ASF1A SMARCD1 SMARCB1 RBM10 KIF11 MAEL BAZ1B CHD3 ESR1 SMARCA1 KAT2B SOX9 MYSM1 ACTL6A |
| | GO: 0031618 | CBX5 NCAPD3 CBX3 |
| | GO: 0031933 | LRWD1 |
| | GO: 0033553 | BAZ2A SUV39H1 SIRT1 RRP8 |
| | GO: 0035327 | EXOSC3 EXOSC10 PSIP1 EXOSC5 EXOSC4 |
| | GO: 0035985 | HMGA1 CDKN2A HMGA2 |

TABLE I-4

Chromatin-related genes

| Unigene Number | GeneBank Number | Shorthand notation | Gene name |
|---|---|---|---|
| Hs.468972 | NM_006015 | ARID1A | B120, BAF250, BAF250a, BM029, C1orf4, P270, SMARCF1 |
| Hs.374043 | NM_015338 | ASXL1 | KIAA0978, MGC117280, MGC71111 |
| Hs.509140 | NM_182648 | BAZ1A | ACF1, DKFZp586E0518, FLJ14383, WALp1, WCRF180, hACF1 |
| Hs.728963 | NM_032408 | BAZ1B | WBSCR10, WBSCR9, WSTF |
| Hs.314263 | NM_013449 | BAZ2A | DKFZp781B109, FLJ13768, FLJ13780, FLJ45876, KIAA0314, TIP5, WALp3 |
| Hs.470369 | NM_013450 | BAZ2B | DKFZp434H071, DKFZp762I0516, FLJ45644, WALp4 |
| Hs.380403 | NM_005180 | BMI1 | FLVI2, BMI1, MGC12685, PCGF4, RNF51 |
| Hs.444200 | NM_182641 | BPTF | FAC1, FALZ, NURF301 |
| Hs.127950 | NM_014577 | BRD1 | BRL, BRPF1, BRPF2, DKFZp686F0325 |
| Hs.75243 | NM_005104 | BRD2 | D6S113E, DKFZp686N0336, FLJ31942, FSH, FSRG1, KIAA9001, NAT, RING3, RNF3 |
| Hs.522472 | NM_007371 | BRD3 | FLJ23227, FLJ41328, KIAA0043, ORFX, RING3L |

TABLE I-4-continued

Chromatin-related genes

| Unigene Number | GeneBank Number | Shorthand notation | Gene name |
| --- | --- | --- | --- |
| Hs.187763 | NM_014299 | BRD4 | CAP, HUNK1, HUNK1, MCAP |
| Hs.437894 | NM_013263 | BRD7 | BP75, CELTIX1, NAG4 |
| Hs.519337 | NM_006696 | BRD8 | SMAP, SMAP2, p120 |
| Hs.482520 | NM_001726 | BRDT | BRD6, CT9 |
| Hs.1004 | NM_004634 | BRPF1 | BR140 |
| Hs.520096 | NM_015695 | BRPF3 | — |
| Hs.654740 | NM_018963 | BRWD1 | C21orf107, FLJ43918, N143, WDR9 |
| Hs.144447 | NM_018117 | WDR11 | BRWD2, DKFZp434L1715, DR11, FLJ42531, WDR15 |
| Hs.170667 | NM_153252 | BRWD3 | BRODL, FLJ33254, FLJ38568, MRX93 |
| Hs.77254 | NM_006807 | CBX1 | CBX, HP1-BETA, HP1Hs-beta, HP1Hsbeta, M31, MOD1, p25beta |
| Hs.381189 | NM_007276 | CBX3 | HECH, HP1-GAMMA, HP1Hs-gamma |
| Hs.714363 | NM_003655 | CBX4 | NBP16, PC2 |
| Hs.349283 | NM_012117 | CBX5 | HP1, HP1A |
| Hs.592201 | NM_014292 | CBX6 | — |
| Hs.356416 | NM_175709 | CBX7 | — |
| Hs.387258 | NM_020649 | CBX8 | PC3, RC1 |
| Hs.269092 | NM_004824 | CDYL | CDYL1, DKEZp586C1622, MGC131936 |
| Hs.373908 | NM_152342 | CDYL2 | FLJ38866, PCCP1 |
| Hs.643465 | NM_001270 | CHD1 | DKFZp686E2337 |
| Hs.220864 | NM_001271 | CHD2 | DKEZp547I1315, DKEZp686E01200, DKEZp781D1727, FLJ38614 |
| Hs.25601 | NM_001005273 | CHD3 | Mi-2a, Mi2-ALPHA, ZFH |
| Hs.162233 | NM_001273 | CHD4 | DKEZp686E06161, Mi-2b, Mi2-BETA |
| Hs.522898 | NM_015557 | CHD5 | DKEZp434N231, KIAA0444 |
| Hs.371979 | NM_032221 | CHD6 | CHD5, KIAA1335, RIGB |
| Hs.20395 | NM_017780 | CHD7 | FLJ20357, FLJ20361, IS3, KAL5, KIAA1416 |
| Hs.530698 | NM_020920 | CHD8 | DKEZp686N17164, HELSNF1, KIAA1564 |
| Hs.59159 | NM_025134 | CHD9 | AD013, CReMM, KISH2, PRIC320 |
| Hs.208597 | NM_001328 | CTBP1 | BARS, MGC104684 |
| Hs.501345 | NM_022802 | CTBP2 | — |
| Hs.368367 | NM_006565 | CTCF | — |
| Hs.503510 | NM_003797 | EED | HEED, WAIT1 |
| Hs.444082 | NM_004456 | EZH2 | ENX-1, ENX1, EZH1, KMT6, KMT6A, MGC9169 |
| Hs.46700 | NM_005537 | ING1 | p24ING1c, p33, p33ING1, p33ING1b, p47, p47ING1a |
| Hs.107153 | NM_001564 | ING2 | ING1L, p33ING2 |
| Hs.489811 | NM_198267 | ING3 | Eaf4, FLJ20089, ING2, MEAF4, p47ING3 |
| Hs.524210 | NM_016162 | ING4 | MGC12557, my036, p29ING4 |
| Hs.645460 | NM_032329 | ING5 | FLJ23842, p28ING5 |
| Hs.292949 | NM_017553 | INO80 | INO80A, INOC1, hINO80 |
| Hs.405610 | NM_015844 | MBD1 | CXXC3, PCM1, RFT |
| Hs.25674 | NM_003927 | MBD2 | DKFZp58600821, DMTase, NY-CO-41 |
| Hs.178728 | NM_003926 | MBD3 | — |
| Hs.35947 | NM_003925 | MBD4 | MED1 |
| Hs.200716 | NM_004992 | MECP2 | AUTSX3, DKFZp686A24160, MRX16, MRX79, MRXS13, MRXSL, PPMX, RS, RTS, RTT |
| Hs.504091 | NM_198971 | HINFP | DKFZp434F162, HiNF-P, MIZF, ZNF743 |
| Hs.525629 | NM_004689 | MTA1 | — |
| Hs.173043 | NM_004739 | MTA2 | MTA2, MTA1L1, PID |
| Hs.159223 | NM_005967 | NAB2 | MADER, MGC75085 |

TABLE I-4-continued

Chromatin-related genes

| Unigene Number | GeneBank Number | Shorthand notation | Gene name |
|---|---|---|---|
| Hs.106861 | NM_022455 | NSD1 | ARA267, DKFZp666C163, FLJ10684, FLJ22263, FLJ44628, KMT3B, SOTOS, STO |
| Hs.189920 | NM_018165 | PBRM1 | BAF180, MGC156155, MGC156156, PB1 |
| Hs.316750 | NM_032673 | PCGF1 | 2010002K04Rik, FLJ43754, MGC10882, NSPC1, RNF3A-2, RNF68 |
| Hs.371617 | NM_007144 | PCGF2 | MEL-18, MGC10545, RNF110, ZNF144 |
| Hs.144309 | NM_006315 | PCGF3 | DKFZp686D20235, DONG1, FLJ36550, FLJ43813, MGC129615, MGC40413, RNF3, RNF3A |
| Hs.500512 | NM_032373 | PCGF5 | MGC16202, RNF159 |
| Hs.335808 | NM_032154 | PCGF6 | MBLR, MGC15678, MGC17541, RNF134 |
| Hs.305985 | NM_004426 | PHC1 | EDR1, HPH1, RAE28 |
| Hs.524271 | NM_198040 | PHC2 | EDR2, HPH2, MGC163502, PH2 |
| Hs.166204 | NM_002636 | PHF1 | MTF2L2, PCL1, PHF2 |
| Hs.516079 | NM_153812 | PHF13 | MGC43399, PHF5, SPOC1 |
| Hs.211441 | NM_005392 | PHF2 | GRC5, JHDM1E, KIAA0662, MGC176680 |
| Hs.502458 | NM_016621 | PHF21A | BHC80, KIAA1696 |
| Hs.254097 | NM_138415 | PHF21B | BHC80L, FLJ34161, PHF4 |
| Hs.348921 | NM_015153 | PHF3 | KIAA0244, MGC142210, MGC142212 |
| Hs.474980 | NM_032758 | PHF5A | INI, MGC1346, Rds3, SAP14b, SF3b14b, bK223H9.2 |
| Hs.356501 | NM_032458 | PHF6 | BFLS, BORJ, MGC14797 |
| Hs.372719 | NM_173341 | PHF7 | DKFZp434L1850, HSPC045, HSPC226, MGC26088, NYD-SP6 |
| Hs.631989 | NM_002931 | RING1 | RING1A, RNF1 |
| Hs.591490 | NM_007212 | RNF2 | BAP-1, BAP1, DING, HIPI3, RING1B, RING2 |
| Hs.298990 | NM_003070 | SMARCA2 | BAF190, BRM, FLJ36757, MGC74511, SNF2, SNF2L2, SNF2LA, SWI2, Sth1p, hBRM, hSNF2a |
| Hs.327527 | NM_003072 | SMARCA4 | BAF190, BRG1, FLJ39786, RTPS2, SNF2, SNF2-BETA, SNF2L4, SNF2LB, SWI2, hSNF2b |
| Hs.558463 | NM_015001 | SPEN | HIAA0929, KIAA0929, MINT, RBM15C, SHARP |
| Hs.462732 | NM_015355 | SUZ12 | CHET9, JJAZ1, KIAA0160 |
| Hs.440382 | NM_006510 | TRIM27 | RFP, RNF76 |
| Hs.446240 | NM_183048 | ZMYND8 | MGC31836, PRKCBP1, PRO2893, RACK7 |
| Hs.534255 | NM_004048 | B2M | — |
| Hs.412707 | NM_000194 | HPRT1 | HGPRT, HPRT |
| Hs.728776 | NM_012423 | RPL13A | L13A, TSTA1 |
| Hs.592355 | NM_002046 | GAPDH | G3PD, GAPD, MGC88685 |
| Hs.520640 | NM_001101 | ACTB | PS1TP5BP1 |

According to the method for constructing the high-throughput sequencing library in the embodiment of the present invention, the high-throughput sequencing library of the genomic DNA sample, especially the high-throughput sequencing library of the specified regions known to have the methylation sites of the genomic DNA sample can be constructed effectively, so that the sequencing library can be applied to high-throughout sequencing technology effectively. The methylation information of the methylation sites of the specified genomic regions can thus be obtained effectively by sequencing the library and by subsequent analysis of the obtained sequencing data, such that the detection of methylation in the specified genomic regions of the genomic DNA sample can be realized.

According to another aspect of the present invention, the present invention provides a method for identifying methylation information in specified genomic regions of a sample. According to an embodiment of the present invention, the method comprises the following steps: constructing a high-throughput sequencing library of the specified genomic regions of the sample according to the method of any claim of claims 1-10 or 12; sequencing the high-throughput sequencing library of the specified genomic regions of the sample to obtain sequencing data; and analyzing the sequencing data to identify the methylation information of the specified genomic regions of the sample.

According to the method for identifying methylation information in the specified genomic regions of a sample in the embodiment of the present invention, the methylation information in the specified genomic regions of the sample can be identified accurately, such that, the detection of methylation in the specified genomic regions of the sample can be realized.

According to another aspect of the present invention, the present invention provides an apparatus for identifying methylation information in specified genomic regions of a sample. According to an embodiment of the present invention, the apparatus comprises: a library constructing unit, which is used for constructing a high-throughput sequencing library of the specified genomic regions of the sample and is provided with specific probes; a sequencing unit, which is connected with the library constructing unit, receives the high-throughput sequencing library of the specified genomic regions of the sample from the library constructing unit, and sequences the high-throughput sequencing library of the specified genomic regions of the sample to obtain sequencing data; and a data analysis unit, which is connected with the sequencing unit, receives the sequencing data from the sequencing unit, and analyzes the sequencing data to identify the methylation information of the specified genomic regions of the sample.

According to the apparatus for identifying methylation information in the specified genomic regions of a sample of the embodiment of the present invention, the methylation information in the specified genomic regions of the sample can be identified accurately and conveniently. The apparatus can be applied to various studies on the methylation in specified genomic regions.

According to another aspect of the present invention, the present invention provides a kit for constructing a high-throughput sequencing library of the specified genomic regions of a sample. According to an embodiment of the present invention, the kit comprises specific probes which are specific for known methylation sites. According to the kit for constructing a high-throughput sequencing library of the specified genomic regions of a sample, a high-throughput sequencing library of the specified genomic regions of a sample can be constructed effectively and conveniently.

The additional aspects and advantages of the present invention will be partly showed in the following description, other part may be obvious by the following description or be understood by the practice of the present invention.

BRIEF DESCRIPTION OF THE DRAWINGS

The above and/or additional aspects and advantages of the present invention will become apparent and more readily appreciated from the following descriptions made with reference the accompanying drawings.

(b) shows the distribution of methylation level in promoter regions of a sample genome according to the method of the embodiment of the present invention;

(c) shows original distribution of specified genomic regions of a sample, reads distribution of a high-throughput sequencing library of the specified genomic regions of a sample and methylation distributions of promoter regions and CpG island regions according to the method of the embodiment of the present invention.

Figure 5:
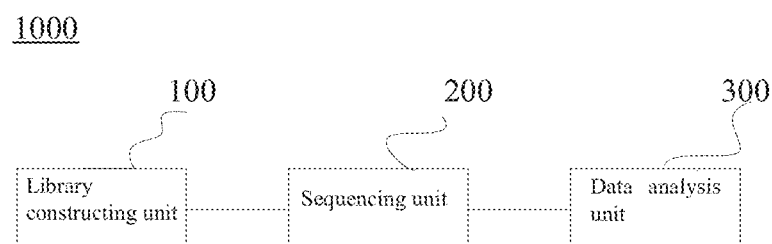

FIG. 5 is a schematic diagram of an apparatus for identifying methylation information of specified genomic regions of a sample according to an embodiment of the present invention.

Figure 6:
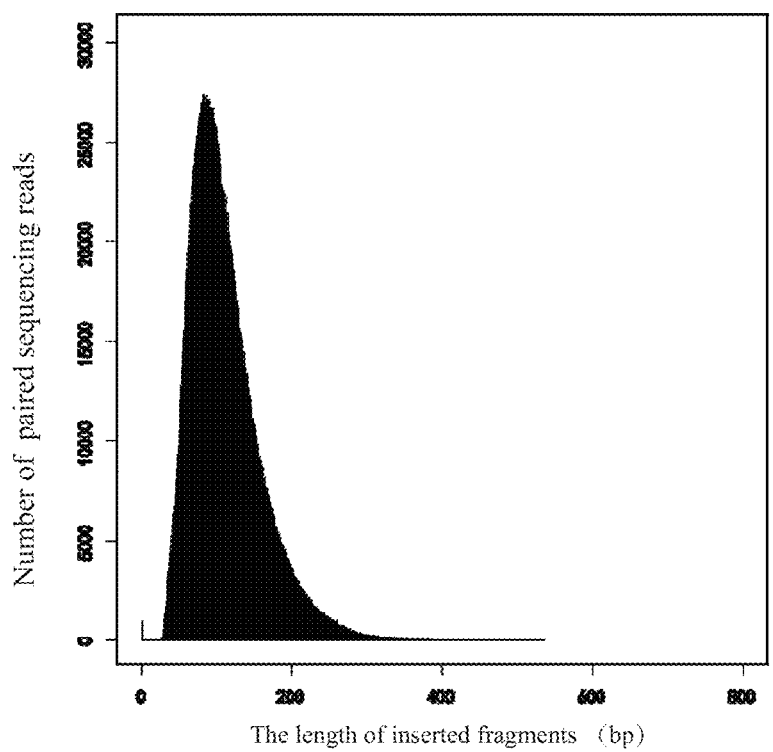

FIG. 6 shows the length distribution of inserted fragments of sequencing reads (it is also referred to as "reads" herein) according to an embodiment of the present invention.

Figure 7:
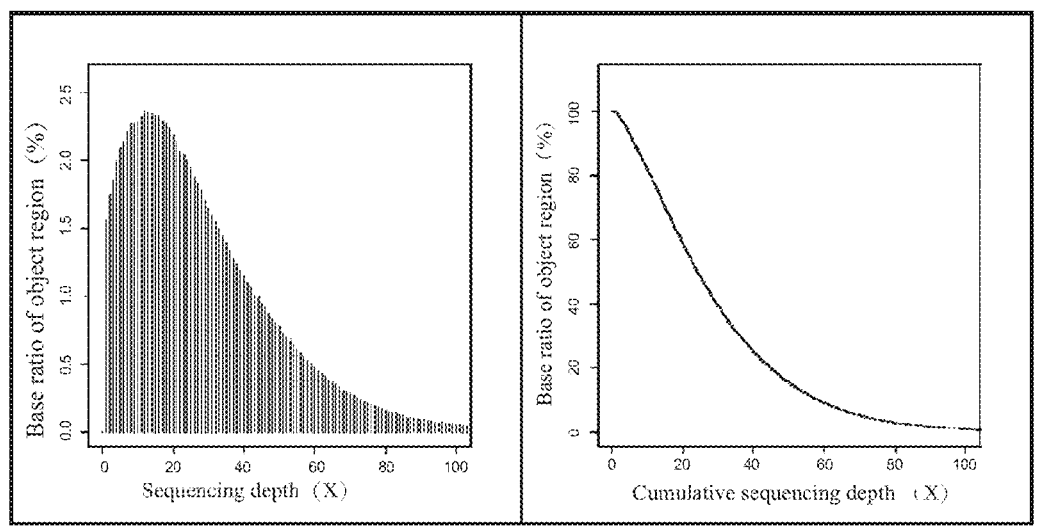

FIG. 7 is a statistical graph of the sequencing depth and the cumulative sequencing depth of each base in captured regions according to an embodiment of the present invention.

Figure 8:
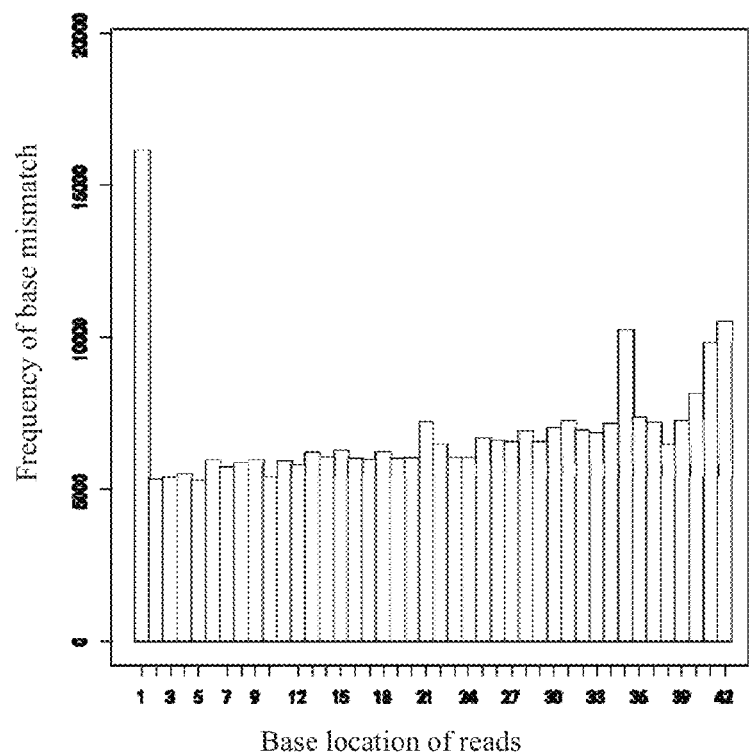

FIG. 8 is a schematic diagram of the frequency of base mismatch at each base position during the process of reads alignment according to an embodiment of the present invention.

Figure 9:
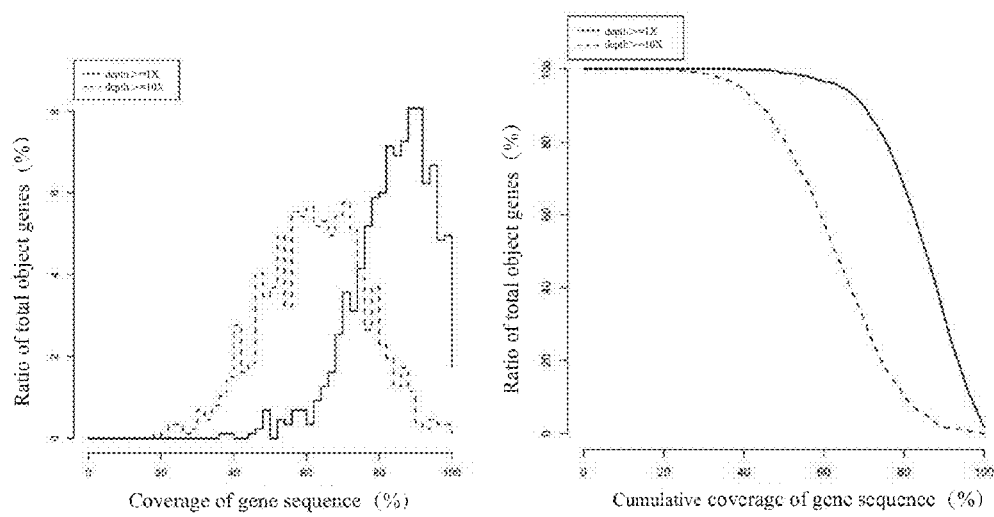
Figure 10:
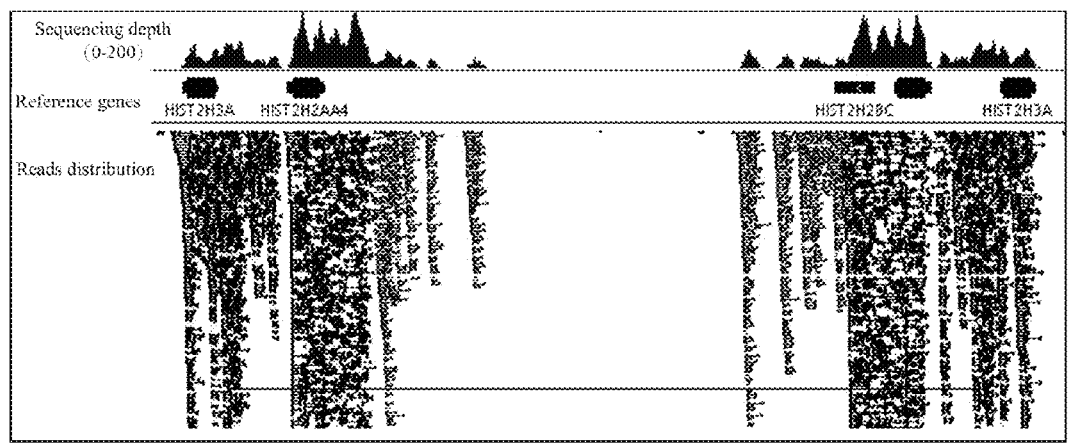

FIG. 9 shows the coverage and the cumulative coverage of each of the captured epigenetic information-related genes of YanHuang cell line at different sequencing depths according to an embodiment of the present invention; and FIG. 10 shows the sequencing coverage of several captured genes according to an embodiment of the present invention.

DETAILED DESCRIPTION OF ILLUSTRATED EMBODIMENTS

Reference will be made in detail to embodiments of the present invention. Examples of the embodiments will be demonstrated in figures. The same or similar elements and the elements having same or similar functions are denoted by like reference numerals throughout the descriptions. The embodiments described herein with reference to drawings are explanatory, illustrative, and used to generally understand the present invention. The embodiments shall not be construed to limit the scope of the present invention.

Method for Constructing High-Throughput Sequencing Library

Figure 1:
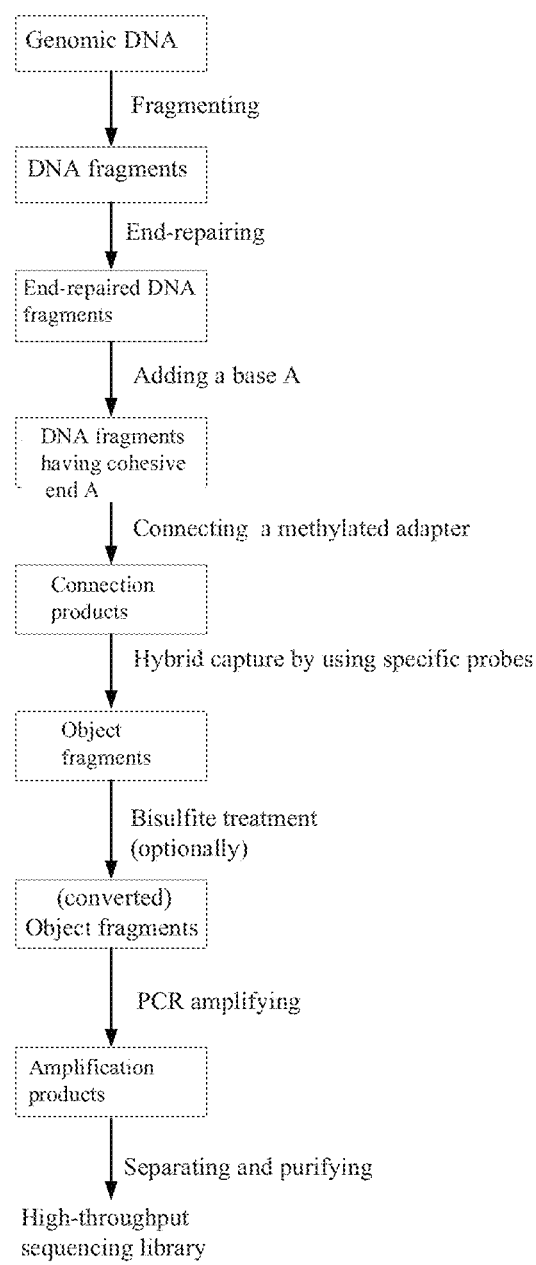
FIG. 1 is a flow chart of a method for constructing a high-throughput sequencing library according to an embodiment of the present invention.

According to one aspect of the present invention, the present invention provides a method for constructing a high-throughput sequencing library. According to an embodiment of the present invention, referring to FIG. 1, the method comprises the following steps:

First of all, a genomic DNA is fragmented to obtain DNA fragments. It is noted that the term "DNA" used herein may be any polymer which comprises deoxyribonucleotides, including but not limited to modified DNA or unmodified DNA. One skilled in the art will appreciate that the source of the genomic DNA is not subjected to special restrictions, the genomic DNA may be obtained by any possible way, it may be directly obtained by commercial way, or be directly obtained from laboratories, or be directly extracted from a sample. According to an embodiment of the present invention, the genomic DNA is extracted from a sample. According to an embodiment of the present invention, the method for constructing a high-throughput sequencing library may further comprises a step of extracting genomic DNA from a sample. According to a specific example of the present invention, the genomic DNA sample may be obtained from at least one of the following: a mammal, a plant and a microorganism. According to an embodiment of the present invention, the mammal may be at least one of human and mouse. According to an embodiment of the present invention, the genomic DNA may be genomic DNA from human whole blood, preferably, may be genomic DNA from peripheral blood mononuclear cells. The inventor of the present invention has found out when the high-throughput sequencing library is constructed by genomic DNA from YH cell, the operation of extracting genomic DNA from the sample may be very convenient, the obtained DNA has a high quality and the methylation information is complete. Therefore, the high-throughput sequencing library of the specified genomic regions of the sample constructed by such genomic DNA can be readily applied to high-throughput sequencing technology, so that the methylation information in the specified genomic regions of the sample can be obtained efficiently based on data analysis of the sequencing result. According to an embodiment of the present invention, the amount of the genomic DNA is not subjected to special restrictions, in an example of the present invention, the amount of the genomic DNA is 2 µg. The inventor of the present invention has surprisingly found out when the amount of the genomic DNA is 2 µg, the high-throughput sequencing library of the specified genomic regions of the sample, which is constructed according to the method for constructing the high-throughput sequencing library in an embodiment of the present invention, can be readily applied to high-throughput sequencing technology, for example, Solexa sequencing technology. Besides, the sequencing result of the library has good accuracy and repeatability the methylation information in the specified regions obtained is accurate and the coverage of methylation sites is high.

Secondly, the DNA fragments are end-repaired to obtain end-repaired DNA fragments. According to an embodiment of the present invention, prior to the step of end repairing, the DNA fragments are purified, which facilitates the subsequent end-repairing step. According to an embodiment of the present invention, Klenow fragment, T4 DNA polymerase and T4 polynucleotide kinase may be used for the end repairing of the DNA fragments, wherein the Klenow fragment has a 5' to 3' polymerase activity and 3' to 5' polymerase activity, but lacks a 5' to 3' exonuclease activity, so that the end of the DNA fragments can be repaired accurately and efficiently. According to an embodiment of the present invention, a step of purifying the end-repaired DNA fragments may be included, which facilitates the subsequent treatments.

Next, a base A is added to the 3' end of the end-repaired DNA fragments to obtain DNA fragments having cohesive end A. According to an embodiment of the present invention, the Klenow (3'-5' exo-), which has a 3' to 5' exonuclease activity, may be used to add a base A to the 3' end of the end-repaired DNA fragments, so that the base A can be added to the 3' end of the end-repaired DNA fragments accurately and efficiently. According to an embodiment of the present invention, a step of purifying the DNA fragments having cohesive end A may be included, which facilitates the subsequent treatment.

Next, the DNA fragments having cohesive end A are ligated with a methylated adapter to obtain connection products. It is noted that the term "methylated adapter" used herein is such an adapter that all C locis of its nucleotide sequence is methylated. According to an embodiment of the present invention, prior to the ligation of the DNA fragments having cohesive end A with the methylated adapter, a step of methylating a sequencing adapter used in conventional sequencing technology may be included. Such that a subsequent bisulfite treatment will not be interfered by the sequencing adapter, for example, the sequence of the sequencing adapter may be converted during the bisulfite treatment. One skilled in the art may appreciate that the method of methylating the sequencing adapter is not subjected to special restrictions, any method for methylating a sequencing adapter in the art can be used.

According to an embodiment of the present invention, a tag may be brought into the methylated adapter, so that the high-throughput sequencing library of the specified genomic regions of a plurality of samples can be constructed conveniently at one time, and can be efficiently applied to a high-throughput sequencing platform. After analysis of the sequencing result and based on the sequence information of the tag, the sequence information of the high-throughput sequencing library of the specified genomic regions of the plurality of samples can be accurately separated among the samples, besides, the methylation information in the specified genomic regions of the plurality of samples can also be accurately separated among the samples. Therefore, it is possible to make full use of the high-throughput sequencing platforms, thereby saving time and lowering the cost.

According to an embodiment of the present invention, the length of the tag is 6 bp, different samples are attached with different tags during the process of constructing the library. Before being captured, a plurality of different libraries are mixed together to form a new library, the new library is then subjected to probes-capture and subsequent sequencing. The sequencing data is a mixed data of the plurality of samples, based on the different tags in each reads (the sequence result read from a sequencer), each sample can be distinguished from others. By using this method, it is possible to lower the costs, time and labor.

According to an embodiment of the present invention, DNA fragments having cohesive end A are connected with the methylated adapter by T4 DNA ligase, such that connection products can be conveniently obtained. According to an embodiment of the present invention, a step of purifying the connection products may be included, which facilitates the subsequent treatment.

Next, hybrid capture is carried out on the connection products by specific probes, so as to obtain object fragments. According to an embodiment of the present invention, the term "specific probe" used herein refers to a probe that is specific for known methylation sites. In an example of the present invention, the specific probes are designed based on using human genome as a reference sequence and using specified genomic regions known to have methylation sites as target sequences. Specifically, the genomic region known to have methylation sites includes at least one of the following: a promoter region, a CpG island region, a CGI shore region, and a imprinted gene region. Therefore, when carrying out the hybrid capture by using the specific probes of the embodiment of the present invention, the sequences in the sample genome which are complimentary to the target sequences, i.e. regions in the sample genome known to have methylation sites (which are also referred to as "specified genomic regions" herein) can be captured efficiently.

According to an embodiment of the present invention, the genomic regions known to have methylation sites and used for designing the specific probes are a coding region or promoter region of at least one of the genes listed in Table I. According to an embodiment of the present invention, the coding region is an exon region, and the promoter region is a region spreading over 2200 bp upstream and 500 bp downstream from the transcription start site. According to an embodiment of the present invention, the specific probes are designed by an eArray system. According to an embodiment of the present invention, optionally, the length of the probes is 12mer.

The genes listed in above Table I is screened out by making use of database resources (such as gene ontology) and by doing a lot of experiments. The inventor of the present invention has surprisingly found out that probes prepared by using these genes can capture the desired target fragments most efficiently, and can facilitate subsequent studies. According to an embodiment of the present invention, a region ranging spreading over 2200 bp upstream and 500 bp downstream from the TSS (transcription start site) can be used as the promoter region, and an exon region can be used as the coding region, the capture probes are designed based on sequence information of these regions. In addition, surprisingly, sequencing results screened by using these gene locus have no coverage bias for each chromosome.

According to the principle of complementary base pairing, a single-stranded capture probe can combined with a single-stranded target sequence complementarily, so as to capture the target region successfully. According to an embodiment of the present invention, the designed probes can be designed as a solid capture chip (wherein the probes are immobilized on a solid support) or be designed as a liquid capture chip (wherein the probes are free in the liquid), however, limited by various factors, such as probe length, probe density and high cost etc., the solid capture chip is rarely used, while the liquid capture chip is preferred in the present invention.

According to an embodiment of the present invention, the probes are designed by an eArray system (a system of probe design) of Agilent Technologies Co., Ltd, the length of the probes is 120mer, the probe can cover a large range of length, ranging from less than 200 kb to 24 mb or longer. The eArray system can make use of a bioinformatics tool, such as Window Masker and Repeat Masker, to analyze and mask object regions, such that, the designing of the probes for these regions can be avoided. Therefore, interferences occurred during the hybrid capture and during the alignment of the sequences will be greatly reduced, in addition, shortening of the coverage on length can lower the cost to some extent.

According to an embodiment of the present invention, compared with normal sequences (the average content of A, T, C, G base is 25%, respectively), GC-rich sequences (the content of GC base is higher than 60%) in nucleic acid may lead to the reduction of capture efficiency because of the molecular structure of C and G base. For the key research regions, for example, CGI regions (CpG Island), it is recommended to design an increased amount of the probes to obtain sufficient and accurate CGI data.

In addition, according to an embodiment of the present invention, prior to the hybrid capture, the method of the present invention may further comprises a step of carrying out a hybrid blocking on the connection products (especially, the repeated regions in the genomic sequence of the connection products) and the methylated adapter of the connection products by single stranded oligonucleotides (for example, $c_o t$-1 DNA and an adapter block). The inventor of the present invention has surprisingly found out that the hybrid capture on the connection products will be significantly enhanced after the connection products (especially the repeated regions in the genomic sequence of the connection products) and methylated adapter of the connection products have been hybrid-blocked by $c_o t$-1 DNA and the adapter block respectively. According to an embodiment of the present invention, the amount of $c_o t$-1 DNA is not subjected to special restrictions. In an example of the present invention, preferably, an excess of the $c_o t$-1 DNA is used to perform the hybrid blocking on the repeated regions in the genomic sequence of the connection products. Wherein the term "excess" used herein means the amount of $c_o t$-1 DNA is much higher than the amount of the connection products to be used in the hybrid capture, that is to say, the amount of $c_o t$-1 DNA may be more than twice the amount of the connection products to be used in the hybrid capture. In an example of the present invention, preferably, the amount of $c_o t$-1 DNA is five times the amount of the connection products to be used in the hybrid capture. In an example of the present invention, if the amount of $c_o t$-1 DNA is less than five times the amount of the connection products to be used in the hybrid capture, the hybrid blocking is not complete, as a result, the nonspecific strong hybrid background signal of the repeated sequences produces a strong interference, which seriously affects the efficiency of nucleic acid hybridization. If the amount of $c_o t$-1 DNA is more than five times the amount of the connection products to be used in the hybrid capture, the combination of the probes and the connection products will be affected by too much $c_o t$-1 DNA, which also seriously affects the efficiency of nucleic acid hybridization. Therefore, when the hybrid blocking on the repeated regions in the genomic sequence of the connection products is carried out by using $c_o t$-1 DNA in an amount of five times the connection products to be used in the carried out hybrid capture, the blocking can be carried out conveniently and efficiently, in the hybrid capture, the repeated DNA sequence can be removed, so that the interference caused by nonspecific strong hybrid background signal of the repeated sequences can be effectively avoided, the efficiency of nucleic acid hybridization is thus significantly improved and the hybridization effect is good. According to an embodiment of the present invention, the adapter block includes at least one of Block 1 and Block 2, so that the methylated adapter of the connection product can be blocked efficiently. According to an embodiment of the present invention, 1 μg of the connection products is used in the hybrid capture, such that the efficiency of hybrid capture is improved. In an example of the present invention in order to efficiently capture object fragments, the step of the hybrid capture on the connection products by the specific probes may further comprises a step of capturing the object fragments by using streptomycin magnetic beads, so as to.

Next, the object fragments are amplified by PCR to obtain amplification products. According to an embodiment of the present invention, the PCR amplification of the converted object fragments is performed by using hot-start taq DNA polymerase. According to an embodiment of the present invention, the type of the hot-start taq DNA polymerase is not subjected to special restriction. In an example of the present invention, the hot-start taq DNA polymerase is r-taq polymerase, so that the PCR amplification is efficient and time-saving.

Finally, the amplification products are separated and purified, the obtained amplification product constitutes a high-throughput sequencing library for detecting whole genome methylation. According to an embodiment of the present invention, the method for separating and purifying the amplification products is not subjected to special restriction. In an example of the present invention, the separation and purification is carried out by using at least one of the following: magnetic beads purification, column purification and 2% agarose gel electrophoresis, wherein the 2% agarose gel electrophoresis is preferred. In an example of the present invention, the length of fragments in the high-throughput sequencing library is 300-450 bp, so that the high-throughput sequencing library can be efficiently applied to a high-throughput sequencing platform, such as Solexa sequencing platform. Besides, the method of the present invention has good repeatability, the sequencing result of the library has good accuracy, and the obtained methylation information of the specified genomic regions specific to the specific probes is complete.

According to an embodiment of the present invention, after the object fragments have been obtained, the object fragments may be treated by bisulfite, such that non-methylated cytosines in the object fragments are converted to uracils, thereby obtaining converted object fragments. According to an embodiment of the present invention, before treating the object fragments with bisulfite, it may further comprises a step of mixing the object fragments with fragmented λ-DNA. The inventor has found out that if exogenous DNA (λ-DNA) is added (i.e., mixing the object fragments with the exogenous DNA), followed by a bisulfate co-treatment, the object fragments can be protected, thereby the damage of bisulfate to trace amount of DNA will be minimized, which further improves the detection precision, so that the detection of methylation in trace amount of the genomic DNA, even at nanogram level (for example, 50-150 ng), is feasible. According to an embodiment of the present invention, the amount of fragmentedλ-DNA added is not subjected to special restrictions. In an example of the present invention, preferably, the amount of the fragmentedλ-DNA is 200-400 ng, more preferably, the amount of the fragmentedλ-DNA is 200 ng. One skilled in the art will appreciate that the fragmentedλ-DNA can be prepared by any known methods in the art, for example, the fragmented λ-DNA can be prepared by using a same method as that used for i fragmentsing the genomic DNA.

Bisulfite treatment can be carried out by any method known in the art, in an example of the present invention, the bisulfite treatment may be carried out by using a commercial kit, and the EZ DNA Methylation-Gold Kit™ (ZYMO)) is preferred. The inventor of the present invention has surprisingly found out that it is convenient and efficient to treat the object fragments with bisulfate by EZ DNA Methylation-Gold Kit™ (ZYMO), the result of the treatment effect is good, and the non-methylated cytosines in the object fragments can be efficiently and accurately converted to uracils, which facilitates subsequent treatments.

Therefore, according to an embodiment of the present invention, after being captured, the object fragments can be sequenced directly, and analysis of single nucleotide polymorphisms (SNPs), mutation, insertion, indel and copy number variation (CNVs) of gene can thus be performed based on the sequencing result. In another embodiment of the present invention, after being captured, the bisulfite treatment and subsequent sequencing are carried out, such that the analysis of DNA methylation can be performed for example, analysis of methylation density, methylation level of different element, cytosine methylation and differentially methylated regions (DMRs).

By using the method for constructing the high-throughput sequencing library according to an embodiment of the present invention, the high-throughput sequencing library of the specified genomic regions of a sample can be efficiently constructed, besides, the library can be efficiently applied to high-throughput sequencing technology. After sequencing the high-throughput sequencing library and then analyzing the sequencing result, the methylation information in the specified genomic regions of the sample can accurately be obtained, thereby realizing the detection of methylation in the specified genomic regions of the sample.

Methods and Apparatus for Identifying Methylation Information in Specified Genomic Regions of a Sample According to another aspect of the present invention, the present invention provides a method for identifying methylation information in specified genomic regions of a sample. According to an embodiment of the present invention, the method comprises the following steps: constructing a high-throughput sequencing library of the specified genome regions of a sample according to the method for constructing a high-throughput sequencing library of an embodiment of the present invention; sequencing the high-throughput sequencing library of the specified genome regions of the sample to obtain sequencing data; analyzing the sequencing data to identify the methylation information in the specified genomic regions of the sample.

According to an embodiment of the present invention, the library is sequenced by using high-throughput sequencing technology. One skilled in the art will appreciate that the library can be sequenced by any high-throughput sequencing technology known in the art. In an example of the present invention, the library is sequenced by Hiseq2000 sequencer. The inventor has found out when using the Hiseq2000 sequencer to sequence the high-throughput sequencing library of the specified genomic regions of a sample, it is efficient and time-saving to obtain the sequencing result, the sequencing result is accurate and the repeatability is good.

According to the method for identifying methylation information in specified genomic regions of a sample of an embodiment of the present invention, the high-throughput sequencing library of the specified genomic regions of the sample can be constructed efficiently, and the library can be sequenced accurately by high-throughput sequencing technology (for example, the Solexa sequencing technology). Based on analysis of the sequencing result, the methylation information in the specified genomic regions of the sample can be identified accurately, so that the detection of methylation in the specified genomic regions of the sample can be realized, a large amount of the methylation sites of the specified regions can be covered and the methylation information is very complete.

According to another aspect of the present invention, the present invention provides an apparatus for identifying methylation information in specified genomic regions of a sample. Referencing to FIG. 5, according to an embodiment of the present invention, the apparatus comprises: a library-constructing unit 100, a sequencing unit 200 and a data analysis unit 300.

According to an embodiment of the present invention, the library-constructing unit 100 is used for constructing a high-throughput sequencing library of specified genomic regions of a sample, wherein specific probes are provided in the library-constructing unit 100. According to an embodiment of the present invention, the specific probes are specific for known methylation sites. According to an embodiment of the present invention, the specific probes are designed based on using human genome as a reference sequence and using the specified genomic regions known to have methylation sites as target sequences, specifically, the genomic region known to have the methylation site includes at least one of the following: a promoter region, a CpG island region, a CGI shore region and an imprinted gene region, therefore, when carrying out hybrid capture by using the specific probes of the embodiment of the present invention, sequences in a DNA sample complementary to the target sequences (i.e., genomic regions in the DAN sample known to have methylation sites) can be captured efficiently. Therefore, the library-constructing unit 100 is suitable for constructing the high-throughput sequencing library. According to an embodiment of the present invention, the genomic region known to have the methylation site and used to design probes is a coding region or promoter region of at least one of the genes listed in Table I. According to an embodiment of the present invention, the coding region is an exon region, and the promoter region is a region spreading over 2200 bp upstream and 500 bp downstream from the transcription start site. According to an embodiment of the present invention, the specific probes are designed by an eArray system. According to an embodiment of the present invention, optionally, the length of the probes is 12mer. The probes have already been described above and will not be repeated herein.

The sequencing unit 200, which is connected to the library-constructing unit 100, receives the high-throughput sequencing library of the specified genomic regions of a sample from the library-constructing unit 100, and sequences the high-throughput sequencing library of the specified genomic regions of the sample to obtain sequencing data.

The data-analysis unit 300, which is connected to the sequencing unit 200, receives the sequencing data from the sequencing unit 200, and analyzes the sequencing data to identify the methylation information in the specified genomic regions of the sample, thereby realizing the detection of methylation in the specified genomic regions of the sample.

One skilled in the art will appreciate that any known apparatus in the art suitable for the above operation may be adopted as a component part of each of the above units. Further, the term "connect" used here shall be interpreted broadly, it may refer to "connect directly", or may refer to "connect indirectly" through a medium, which will be determined through the context by one skilled in the art.

By using the apparatus for identifying the methylation information in the specified genomic regions of the sample according to an embodiment of the present invention, it is convenient and accurate to identify the methylation information in the specified genomic regions of a sample. Therefore, the apparatus can be used for various methylation researches on specified genomic regions, for example, the specified genomic region may be genomic region known to have methylation site, and the methylation research may be the detection of methylation abnormalities in the specified genomic region.

Kit

According to another aspect of the present invention, the present invention provides a kit for constructing a high-throughput sequencing library of specified genomic regions of a sample. According to an embodiment of the present invention, the kit comprises: specific probes, which are specific for known methylation sites. In an example of the present invention, the specific probes are designed based on using human genome as a reference sequence and using specified genomic regions in the human genome known to have methylation sites as target sequences, specifically, the genomic region known to have the methylation site includes at least one of the following: a promoter region, a CpG island region, a CGI shore region and an imprinted gene region. Therefore, when carrying out the hybrid capture by using the specific probes of the embodiment of the present invention, the sequences in the DNA sample which are complementary to the target sequences, i.e., regions in the DAN sample known to have methylation sites, can be captured efficiently. According to an embodiment of the present invention, the genomic region known to have the methylation site and used for designing the specific probes is a coding region or promoter region of at least one of the genes listed in Table I. According to an embodiment of the present invention, the coding region is an exon region, and the promoter region is a region spreading over 2200 bp upstream and 500 bp downstream from the transcription start site. According to an embodiment of the present invention, the specific probes are designed by an eArray system. According to an embodiment of the present invention, optionally, the length of the probes is 12mer. The probes have already been described above and will not be repeated herein.

One skilled in the art will appreciate that the kit may further comprise other components required for constructing the high-throughput sequencing library of the specified genomic regions of the sample, detailed description of the components will not be discussed herein. By using the kit for constructing the high-throughput sequencing library of the specified genomic regions of the sample of an embodiment of the present invention, the high-throughput sequencing library of the specified genomic regions of the sample can be constructed efficiently.

It should be noted that the method of constructing the high-throughput sequencing library of the specified genomic regions of the sample and use thereof according to the embodiments of the present invention is obtained through creative work and the technical solutions of the present invention have been optimized through hard work by the inventors of the present invention.

Reference will be made in detail to embodiments of the present invention. It would be appreciated by those skilled in the art that the following embodiments are explanatory, and cannot be construed to limit the scope of the present invention. Detailed experimental methods or conditions that are not indicated in the following examples have been described in well-known literatures in the art (for example, J. Sambrook, et al., Molecular Cloning Laboratory Manual, translated by Huang PT, third version, Science Press) or in standard protocols of instruments or reagents. Reagents or instruments not indicated any manufacturer are commercially common, for example, they can be purchased from Illumina company.

EXAMPLE 1

In example 1, 2 μg of genomic DNA from human peripheral blood mononuclear cells was used as a sample, the following steps were then performed.

I. Fragmentation of Genomic DNA

The genomic DNA sample was fragmented by a Covaris-S2 instrument according to the parameters in the following table, such that DNA fragments were obtained.

| | | |
|---|---|---|
| Treatment 1 | Load ratio (%) | 10 |
| | Intensity | 5 |
| | Cycle/burst | 200 |
| | Time (s) | 50 |
| Treatment 2 | Time (s) | 0 |
| Treatment 3 | Time (s) | 0 |
| Treatment 4 | Time (s) | 0 |
| | Cycle | 3 |

The obtained DNA fragments were then subjected to agarose gel electrophoresis, the length of the DNA fragments were kept in the range of 150-300 bp, without protein contaminant or RNA contaminant. After purification with QIAquick PCR purified kit (Qiagen) or magnetic beads, qualified DNA fragments were dissolved in 32 µl of elution buffer, and reserved for further use.

The same method was used to prepare 200-400 ng of fragmented λ-DNA, wherein the λ-DNA was exogenous and non-methylated.

II. End Repair

1) An end-repairing reaction system including the DNA fragments obtained in step 1 was formulated in a 1.5 ml centrifuge tube according to the following parameters:

| | |
|---|---|
| DNA fragments | 30 µL |
| H$_2$O | 45 µL |
| 10x polynucleotide kinase buffer | 10 µL |
| dNTPs (each component was 10 mM) | 4 µL |
| T4 DNA polymerase | 5 µL |
| Klenow fragments | 1 µL |
| T4 polynucleotide kinase | 5 µL |
| Total volume | 100 µL |

2) The above reaction system was incubated in Thermomixer (Eppendorf) at 20☐, for 30 min. After purification with QIAquick PCR purified kit (Qiagen), the purified products were dissolved in 34 µl of elution buffer.

III. Addition of a Base A

1) An reaction system for the addition of base A including the DNA products obtained in step 2 was formulated in a 1.5 ml centrifuge tube according to the following parameters:

| | |
|---|---|
| DNA | 32 µL |
| 10x Blue buffer | 5 µL |
| dATP(diluted tol mM, GE Company) | 10 µL |
| Klenow (3'-5' exo-) | 3 µL |
| Total volume | 50 µL |

2) The above reaction system was incubated in Thermomixer (Eppendorf) at 37☐, for 30 min. After purification with MiniElute PCR purified kit (Qiagen), purified products were dissolved in 20 µl of elution buffer.

IV. Linkage of a Methylated Adapter

1) An linkage reaction system for the linkage of a methylated:adapter (which is also referred to as "barcode-containing methylated adapter") including the DNA products obtained in step 3 was formulated according to the following parameters:

| | |
|---|---|
| DNA | 18 µL |
| 2 × Rapid linkage buffer | 25 µL |
| Barcode-containing methylated adapter* | 4 µL |
| T4 DNA ligase (Rapid, L603-HC-L) | 3 µL |
| Total volume | 50 µL |

*The sequences of the methylated adapter were:
adapter 1: 5'Phos/GATCGGAAGAGCACACGTCTGAACTCCAGTCAC (SEQ ID NO: 1)
adapter 2: 5'TACACTCTTTCCCTACACGACGCTCTTCCGATCT (SEQ ID NO: 2)
or a pooling hybrid was performed by using the following barcode-containing methylated adapters:
adapter 1': 5'Phos/<u>NNNNNN</u>AGATCGGAAGAGCACACGTCTGAACTCCAGTCAC (SEQ ID NO: 3)
adapter 2': 5'TACACTCTTTCCCTACACGACGCTCTTCCGATCT<u>NNNNNNN</u>T (SEQ ID NO: 4)
Wherein all of the base C in the adapter 1 and adapter 2 or adapter 1' and adapter 2' were protected by methylation.

2) The above reaction system was incubated in Thermomixer (Eppendorf) at 20° C., for 15 min to obtain connection products. After purification with MiniElute PCR purified kit (Qiagen), the purified connection products were dissolved in 22 µl of elution buffer.

V. Hybrid Capture for Object Fragments

1. Designing of specific probes: a group of specific probes without complementary sequence was designed by using SSAHA algorithm. Specifically, the probes were designed by using human genome hg19 as a reference sequence and selecting about 10,000 promoter regions, 28,000 CpG island regions, 28,000 CGI shore regions and 61 imprinted gene regions that were known to have methylation sites as target sequences, as for regions less than 200 bp were revised to 200 bp in length by filling, and overlapping regions were removed. The sequences of the probes had to meet the following requirements: no overlapping sequence exist, all probes must be sequences without complementary sequence even if up to 5 bases were inserted, deleted or mismatched, and the each of the synthesized DNA probes has to be coupled with biotin as a marker for subsequent capture procedure. The designed specific probes were then prepared by Roche NimbleGen, and were reserved for further use.

Table 1 shows the evaluation result of coverage over the target regions by the specific probes according to an embodiment of the present invention. It can be seen from Table 1 that the probes almost cover all the promoter regions, and most of the imprinted gene regions, CpG island regions and CGI shore regions in the genome. The inventor has found out that most of the uncovered regions are regions having a certain number of repeated short sequences, if these regions are captured by probes, it will increase too much data information of non-target regions, besides, the existence of the repeated sequences may influence the capture for other regions. Because little methylation information is contained in these repeated regions and the overall methylation level will not be significantly affected by these regions, these regions will not be used as target sequences of the probes in the present invention.

2. Hybridization

1) A hybridization reaction system including the connection products obtained in above step 4 was formulated according to the following parameters.

The connection products were quantified by using Qubit fluorometer and corresponding Quant-iT dsDNA HS detection kit (Invitrogen), 1 µg of the connection products was then added in a new 1.5 ml EP tube, and to which 10 µL of 1 mg/mL c$_o$t-1 DNA and 1 nmol of adapter block were also added. The EP tube was dried at 60° C. by SpeedVac, and was reserved for further use. Then, 2×SC hybridization buffer and SC hybridization composition A were added to the dried EP tube respectively.

| | |
|---|---|
| c₀t-1 DNA | 5 µg |
| Connection products | 1 µg |
| Adapter block Block1 and Block2* | 1 nmol, respectively |
| 2 × SC hybridization buffer | 7.5 µL |
| SC hybridization composition A | 3 µL |
| Total volume | 10.5 µL |

*The sequences of the adapter blocks were:
Block1: 5'GTGACTGGAGTTCAGACGTGTGCTCTTCCGATC (SEQ ID NO: 5)
Block2: 5'AGATCGGAAGAGCGTCGTGTAGGGAAAGAGTGTA (SEQ ID NO: 6)
Optionally, a pooling hybrid was performed by using the following adapter blocks:
Block1': 5'GTGACTGGAGTTCAGACGTGTGCTCTTCCGATCTNNNNNN (SEQ ID NO: 7)
Block2': 5'ANNNNNNAGATCGGAAGAGCGTCGTGTAGGGAAAGAGTGTA (SEQ ID NO: 8)
Wherein the bases NNNNNN in Block1' and Block2' were respectively complementary with the N bases in adapter 1' and adapter 2'.

The above reaction system was mixed and centrifuged at full speed for 10 s in a centrifuge, then transferred to heat block and incubated at 95□, for 15 min to denature DNA.

4) The above reaction sample was taken out and mixed by vibrating, centrifuged at full speed for 10 s, transferred to 0.2 mL of PCR tube or 96-well PCR plate, and to which 4.5 µL of above-mentioned probes library was added, and mixed by vibrating. After centrifuged at full speed for 10 s on centrifuge, the PCR tube or 96-well PCR plate was placed in PCR amplifier, such that the reaction sample hybridized at 47□, for 64 h-72 h, wherein the hot lid temperature of the PCR amplifier was 57□.

3. Sequence Capture

1) Preparing Washing Buffer a) The following four washing buffers: 10×SC washing buffer I, 10×SC washing buffer I, 10×SC washing buffer III and 2× Stringent washing buffer were diluted to 1× buffer and then stored, wherein the storage time should not exceed 2 weeks.

b) The prepared 1 ml of Stringent washing buffer and 1 ml of SC washing buffer I were preheated at 47□, respectively.

2) Preparing Streptomycin Magnetic Beads a) The Dynabeads M-280 Streptavidin (Invitrogen) magnetic beads were taken out from a fridge and mixed thoroughly, then 100 µL of the magnetic beads was placed in a 1.5 ml EP tube;

b) The EP tube was placed on a magnet until the solution was clear, the supernatant was removed by a pipettor, and 200 µL of Streptavidin Dynabead washing buffer was then added;

c) The above reaction system was vibrated (Vortex) for 10 s and mixed thoroughly, then the EP tube was placed on a magnet again until the solution was clear, and the supernatant was removed by a pipettor;

d) The reaction system obtained in above step c) was washed for twice;

e) The magnetic beads of above reaction system were resuspended by 100 µL of Streptavidin Dynabead washing buffer, and then the reaction system was transferred to a 0.2 mL EP tube;

f) The EP tube was placed on a magnet until the solution was clear, and the supernatant was removed by a pipettor.

3) Capturing Object Fragments by Streptomycin Magnetic Beads

The hybridization mixture was sucked out (the remained volume after hybridization was recorded), to which the prepared magnetic beads were added, after mixed for 10 times by a pipettor, the EP tube was placed in a PCR amplifier, the reaction system was incubated at 47□, for 45 min (wherein the hot lid temperature of the PCR amplifier was 57□, the reaction system was taken out and mixed for 3 s every 15 min to prevent the magnetic beads from precipitating).

4) Washing the Streptomycin Magnetic Beads that have been Combined with Captured DNA a) After incubated for 45 min, the mixture was transferred from the 0.2 mL EP tube to a 1.5 mL EP tube, the 1.5 mL EP tube was then placed on a magnet until the solution was clear, and the supernatant was removed;

b) 100 µL of SC washing buffer I which had been preheated to 47□ was added, the reaction system was vibrated and mixed for 10 s, the EP tube was then placed on a magnet again until the solution was clear, and the supernatant was removed;

c) The EP tube was taken down from the magnet, to which 200 µL of 1× Stringent washing buffer which had been preheated to 47□ was added, the reaction system was then mixed for 10 times by a pipettor (the operation should be quick to prevent the temperature of the solution in the EP tube below 47□);

d) After incubated at 47□ for 45 min, the EP tube was placed on a magnet until the solution was clear, and the supernatant was removed;

e) Steps c)-d) were repeated, and the magnetic beads were washed twice by 1× Stringent washing buffer;

f) 200 µL of 1× washing buffer I at ambient temperature was added, and the reaction system was vibrated and mixed for 2 min (if the solution spattered on the tube cap, flick the EP tube by finger to make the solution fall to the bottom of the tube), the EP tube was then placed on magnet again until the solution was clear, and the supernatant was removed;

g) 200 µL of 1× washing buffer II at ambient temperature was added, and the reaction system was vibrated and mixed for 1 min, the EP tube was then placed on a magnet again until the solution was clear, and the supernatant was removed;

h) 200 µL of 1× washing buffer III at ambient temperature was added, and the reaction system was vibrated and mixed for 30 s, the EP tube was then placed on magnet again until the solution was clear, and the supernatant was removed;

5) Eluting the Streptomycin Magnetic Beads that have been Combined with Object Fragments a) 50 µL of SureSelect washing buffer was added to the above EP tube containing washed magnetic beads, the EP tube was vibrated for 5 s, and the magnetic beads were then resuspended;

b) The above reaction system was incubated at ambient temperature for 10 min, the EP tube was then placed on a magnet for 5-10 min until the solution was clear;

c) The supernatant was transferred to a new 1.5 mL centrifuge tube by a pipettor (at this time, captured DNA was contained in the supernatant, and the magnetic beads could thus be discarded);

d) 50 µL of SureSelect neutralization buffer was added to the supernatant, and mixed;

e) After purified by MiniElute PCR purification kit (Qiagen), the purified products were dissolved in 22 µl of elution buffer.

VI. Bisulfite Treatment 200-400 ng of-prepared fragmented λ-DNA was used as exogenous DNA, a mixture of the captured object fragments and the exogenous DNA were subjected to a bisulfite co-treatment by using EZ DNA Methylation-Gold Kit™ (ZYMO). Detailed steps are as follows:

1) Preparing a solution of CT Conversion Reagent: the CT Conversion Reagent (a solid mixture) was taken out from kit, to which 900 µL of water, 50 µL of M-dissolving buffer and 300 μL of M-dilution buffer were added, then dissolved at ambient temperature and vibrated or shaked on a shaking table for 10 min.

2) Preparing M-washing buffer: 24 mL of 100% ethanol was added to M-washing buffer, and reserved.

3) The object fragment DNA to be converted and λ-DNA were both added to a same PCR tube, if the volume of the reaction system was less than 20 μL, water was used to top up.

4) 130 μL of CT conversion agent was added to the PCR tube. The sample was mixed by slightly tapping the tube or pipettor operation.

5) The sample tube was placed in a thermal cycler, then detailed operations were as follows: placing at 98□ for 5 minutes, and then at 640 for 2.5 hours, after that, the following operations was carried out immediately or the sample tube was stored at 4□ (for at most 20 hours).

6) 600 μL of M binding buffer was fed to Zymo-Spin ICPTMP column, and the column was placed in a collecting tube.

7) The sample to be treated with bisulfite was packed into Zymo-Spin IC™ Column comprising M-binding buffer. Lid the column and overturn the column for several times to mix the sample.

8) The column was centrifuged at full speed (>10,000×g) for 30 seconds to remove effluent.

9) 100 μL of M-washing buffer was fed to the column, and the column was centrifuged at full speed (>10,000×g) for 30 seconds.

10) 200 μL of M-Desulphonation was fed to the column, after left at room temperature for 15 minutes, the column was centrifuged at full speed for 30 seconds to remove effluent.

11) 200 μL of M-washing buffer was fed to the column, and the column was centrifuged at full speed for 30 seconds to remove effluent. The step was repeated once.

12) 12 μL of M-eluting buffer was fed to the matrix of the column, the column was placed in a 1.5 ml EP tube, after left at ambient temperature for 2 min, the object fragments DNA were eluted by means of centrifuging (>10,000×g) at full speed.

VII. PCR Amplification and Purification of Amplification Products

1) The PCR reaction system including the object fragments obtained in step 6 was formulated according to the following system:

```
Object DNA fragments                        10  μL
dNTP (each component was 2.5 mM)             4  μL
10 × PCR buffer                              5  μL
JumpStart Taq DNA polymerase               0.5  μL
P1 primer*                                   1  μL
Tag N**                                      1  μL
dH2O                                      28.5  μL Total volume                                50  μL
```

*wherein, the sequence of P1 primer was: AATGATACGGCGACCAC-CGAGATCTACACTCTTTCCCTACACGACGCTCTTCCGATCT (SEQ ID NO: 9)
**the sequence of tag N was: CAAGCAGAAGACGGCATACGAGAT NNNNNNGTGACTGGAGTTCAGACGTGTGCTCTTCCGATCT (SEQ ID NO: 10), wherein base N was any combination of base A, T, C and G, and was used as a barcode.

The following PCR amplification procedure was performed:

```
94□      1 min
94□     30 s
```

| 58□ | 30 s    |           |
|-----|---------|-----------|
| 72□ | 30 s    | 18 cycles |
| 72□ | 5 min   |           |
| 12□ | storing |           |

2) The PCR amplification products were separated by using 2% agarose gel electrophoresis, and fragments having a length in the range of 300-450 bp in the library were recovered by QIAquick PCR purified kit (Qiagen), and stored for further use.

VIII. Evaluation of the Library

The length and amount of inserted fragments in the library were evaluated by using Bioanalyzer analysis system (Agilent, Santa Clara, USA), and the concentration of the library was accurately quantified by Q-PCR.

Thereby, after the evaluation, the constructed high-throughput sequencing library of specified genomic regions of the sample that was eligible was reserved for further use.

EXAMPLE 2

The high-throughput sequencing library of specified genomic regions of the sample constructed in example 1 was sequenced by Hiseq2000 sequencer with double-end reads of 90 bp.

Raw data was obtained directly after sequencing, and the above-mentioned sequencing result could be obtained by analyzing the raw data, wherein the analytic process mainly included the following steps: firstly, distinguishing library data of different samples by different adapters or sequence barcodes in the PCR primer; next, removing contaminated data and adapter, and filtering out low-quality reads from the raw data; finally, converting base after the above data processing, specifically, all of base C in plus chains was converted to base T, and all of base G in complementary chains was converted to base A. Thereby, the sequencing result of the high-throughput sequencing library of specified genomic regions of the sample constructed in example 1 was obtained.

The obtained sequencing result was analyzed, such that methylation information in the specified genomic regions of the sample could be identified. Wherein the data analysis method comprised: matching reads of the sequencing result back to the reference genome by SOAP2.01 software, wherein the permitted mismatch ratio was 2, such that the unique mapped reads could be identified. Based on the data analysis of the reads, the sequence information and methylation information of specified genomic regions of the sample were obtained.

According to an aspect of the example, single base C of a non-CpG region was served as a standard to calculate conversion ratio of bisulfate treatment in example 1; and sequencing depth and coverage were also analyzed based on the sequencing result. In this example, the coverage of all of the promoter regions, CpG island regions, CGI shore regions and imprinted gene regions, and cover depth of different regions were analyzed, such that methylation level of different regions could be identified.

Figure 2:
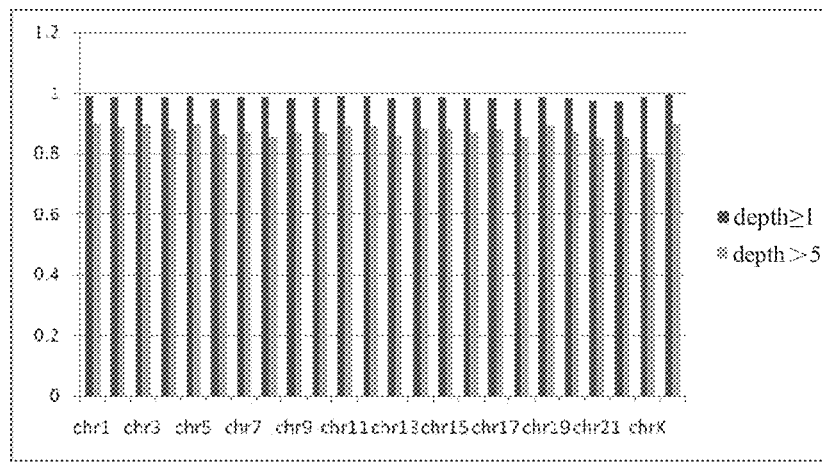
FIG. 2 shows the percentage of captured regions in probe-targeted regions in each chromatin under different cover depths (cover depth ≥1 and cover depth >5) when identifying methylation information in specified genomic regions according to a method of an embodiment of the present invention.

In addition, based on the sequencing result, capture ratio of the specific probes of example 1 was identified in the example. FIG. 2 shows the percentage of captured regions in probe-targeted regions in each chromatin under different cover depths (cover depth ≥1 and cover depth >5) when identifying methylation information in specified genomic regions according to a method of an embodiment of the present invention. FIG. 2 is based on the following sequencing data: the raw reads is 25.5M; the alignment ratio is 75.27%; the unique mapped reads is about 14.9M; and the unique alignment ratio is 57.78%. It can be seen from FIG. 2 when the cover depth is greater than or equal to 1, 99% of the probes can detect methylation information of the captured regions thereof; and when the cover depth is greater than 5, 90% of the probes can detect methylation information the captured regions thereof. It also can be seen from FIG. 2 that actual detection range of the probes can be further improved by appropriately increasing the amount of sequencing data. Therefore, the probes of the example of the present invention can steadily capture target regions, and can accurately detect methylation by combination with bisulfite treatment.

Figure 3:
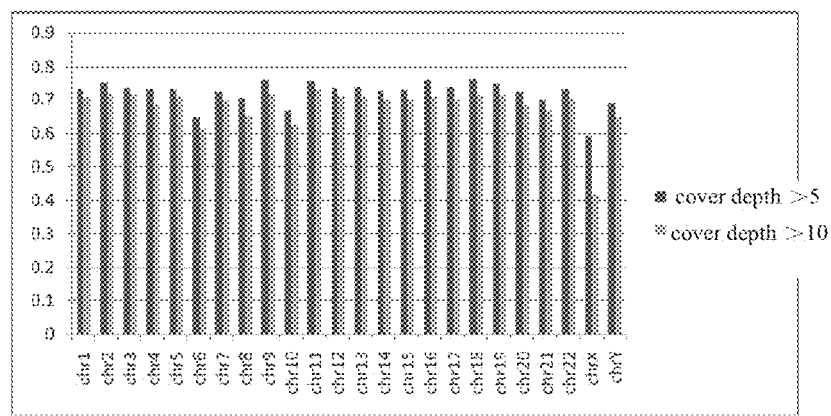
FIG. 3 shows the percentage of promoters detected with methylation information in total promoters in each chromatin under different cover depths when identifying the methylation information in specified genomic regions according to a method of an embodiment of the present invention.

In addition, the example had also analyzed the percentage of different elements detected with methylation information in the genomic region, analysis result was shown in FIG. 3 and Table 2. After hybrid capture and bisulfite treatment, FIG. 3 and Table 2 were obtained by analyzing the following sequencing data and plotting: the raw reads is 25.5M; the alignment ratio is 75.27%; the unique mapped reads is about 14.9M; and the unique alignment ratio is 57.78%. FIG. 3 shows the percentage of promoters detected with methylation information in total promoters in each chromatin under different cover depths when identifying the methylation information in specified genomic regions according to a method of an embodiment of the present invention. It can be seen from FIG. 3 when the cover depth is greater than 5, the percentage of the promoters detected with methylation information in total promoters in each chromatin is greater than 70%, the value is close to theoretical value; and when the cover depth is greater than 10, the percentage of the promoters detected with methylation information in total promoters in each chromatin is greater than 60%. Table 2 shows the distribution of detected imprinted genes in each chromatin when identifying the methylation information in specified genomic regions according to a method of an embodiment of the present invention. It can be seen from Table 2, when the cover depth is greater than or equal to 1, methylation information of 97.6% of imprinted genes can be detected, and when the amount of sequencing data remains unchanged, the number of detected genes significantly reduces as the cover depth increases, which indicates that when analyzing methylation information of imprinted genes under high sequencing depth, it should increase the amount of current sequencing data, so as to increase cover depth of each imprinted gene.

Figure 4:
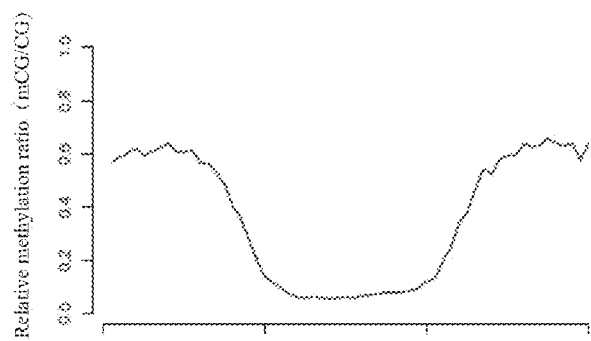
FIG. 4 shows the distribution of methylation level in promoter regions, CpG island regions, exterior regions of CpG island (it is also referred to as CGI shore herein) and imprinted gene regions of the genome when identifying the methylation information of the specified genomic regions according to a method of an embodiment of the present invention; wherein (a) shows the distribution of methylation level in CpG islands and CpG shore regions of a sample genome according to the method of the embodiment of the present invention.
Figure 4:
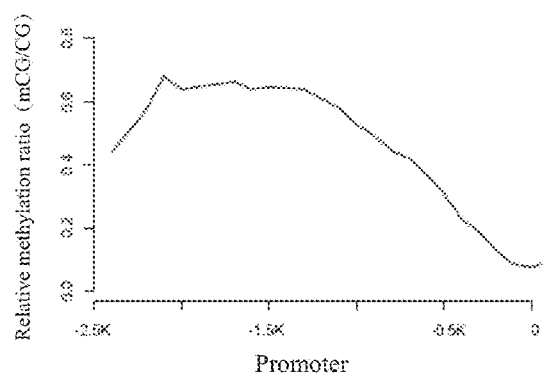
Figure 4:
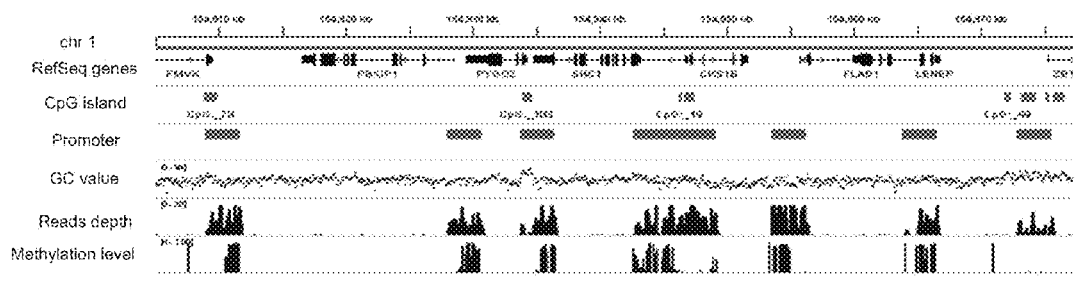

In addition, the distribution of methylation level of promoter regions, CpG island regions, CGI shore regions and imprinted gene regions in genome was also analyzed in this example, the analysis result was showed in FIG. 4.

TABLE 1

The coverage information of the designed probes in each target region of whole genome

| Name of target regions | Amount of target regions | Amount of covered target regions | Coverage ratio of probes (%) |
|---|---|---|---|
| Promoter | 10018 | 9449 | 94.32 |
| imprinted gene | 61 | 41 | 67.21 |
| CpG island | 27623 | 11990 | 43.41 |
| CGI shore | 27628 | 11076 | 40.09 |

TABLE 2

The distribution analysis of detected imprinting genes in each chromatin

| Chromatin | Total number of imprinted genes in each chromatin | Number of detected imprinted genes (≥□x) | Number of detected imprinted genes (≥x) |
|---|---|---|---|
| chr1 | 2 | 2 | 0 |
| chr4 | 1 | 1 | 0 |
| chr6 | 4 | 4 | 0 |
| chr7 | 12 | 12 | 2 |
| chr8 | 2 | 2 | 0 |
| chr9 | 1 | 1 | 0 |
| chr10 | 1 | 1 | 0 |
| chr11 | 11 | 11 | 4 |
| chr12 | 1 | 1 | 1 |
| chr14 | 2 | 2 | 1 |
| chr15 | 15 | 13 | 0 |
| chr16 | 1 | 1 | 0 |
| chr18 | 1 | 1 | 1 |
| chr19 | 2 | 2 | 0 |
| chr20 | 5 | 5 | 3 |
| Sum | 61 | 59 | 12 |

Wherein, FIG. 4(a) shows the distribution of methylation level in CpG islands and CpG shore regions of a sample genome according to the method of the embodiment of the present invention. It can be seen from FIG. 4(a) that methylation level of CG-rich CpG island is low, but methylation level of CpG shore region is significantly higher than methylation level of CpG island. FIG. 4 (b) shows the distribution of methylation level in promoter regions of a sample genome according to the method of the embodiment of the present invention. It can be seen from FIG. 4(b) that in promoter regions, methylation level of transcription initiation site is low, all results are consistent with expected results. FIG. 4(c) shows original distribution of specified genomic regions of a sample, reads distribution of a high-throughput sequencing library of the specified genomic regions of a sample and methylation distribution of promoter regions and CpG island regions according to the method of the embodiment of the present invention. It can be seen from FIG. 4(c) that the method for identifying methylation information in specified genome regions of a sample according to an embodiment of the present invention can effectively capture each specified region and accurately detect methylation information in each region.

EXAMPLE 3

The steps of example 1 was repeated by using a sample of YH cell line (Jun Wang et al. 2008) except that the genomic regions known to have methylation sites and used for designing specific probes were a coding region or promoter region of the genes listed in Table I (there was a total of 867 genes after the repeated genes have been merged), and the probes were designed by using eArray system and were prepared by Agilent Corporation, the length of the probes was 12mer. In addition, the re-sequencing library and non-methylated library were not treated with bisulfite.

Mixed barcodes were used in sequencing, the length of reads was 49 bp and the length of the barcode was 6 bp. 2.67 Mb pairs of sequencing reads and about 240 Mb of sequencing data were obtained. The sequencing reads that have been filtered to remove low-quality sequencing reads and contaminated adapters were aligned to whole genome of human. The alignment result was preliminary analyzed.

Detection Result:

Table 3 shows exact amount of total sequencing data of YH cell line sample, and amount of total data after filtration and screening, number of total reads aligned back to human genome, alignment ratio and ratio of chip capture et al.

TABLE 3

Statistics on sequencing data and alignment data

| Statistical item | Data |
|---|---|
| Number of base in target regions (Mb) | 3.413 |
| Number of raw sequencing reads (n) | 5520814 |
| Amount of raw sequencing data (bp) | 231874188 |
| Number of reads after filtration(n) | 5376398 |
| Amount of available sequencing data (bp) | 225777680 |
| Average length of sequence fragments (bp) | 41.99 |
| Ratio of base of which the quality value is greater than 20 (%) | 99.31 |
| Number of reads aligned to genome (n) | 5283168 |
| Alignment ratio(%) | 98.68 |
| Number of unique mapped reads (n) | 4762261 |
| unique alignment ratio (%) | 88.88 |
| Number of reads aligned to target regions (n) | 2480823 |
| Capture ratio (%) | 52.09 |
| Average depth | 28.9387 |
| Coverage (%) >=1X | 98.67 |
| Coverage (%) >=10X | 81.26 |
| Coverage (%) >=30X | 39.75 |
| Ratio of repeted sequences (%) | 0.34 |

Table 4 shows the depth and coverage of statistical target regions in each chromosome and gene element, viewed as a whole, there was no difference in the coverage of captured target regions among different chromosomes.

TABLE 4

Distribution of mapped reads in each chromosome

| | Exon | | | Promoter | | |
|---|---|---|---|---|---|---|
| | Average | Coverage | | Average | Coverage | |
| Chromosome | depth | >=1X | >=10X | depth | >=1X | >=10X |
| chr1 | 32.5643 | 99.11 | 85.5 | 31.6014 | 99 | 84.42 |
| chr2 | 28.6142 | 98.73 | 81.83 | 29.2488 | 99.21 | 84.77 |
| chr3 | 30.1881 | 98.94 | 84.73 | 28.2216 | 99.2 | 82.6 |
| chr4 | 28.2252 | 98.77 | 82.62 | 28.186 | 99.13 | 83.39 |
| chr5 | 30.552 | 98.54 | 84.1 | 30.092 | 99.32 | 86.92 |
| chr6 | 33.0796 | 98.29 | 85.21 | 34.0625 | 99.54 | 85.72 |
| chr7 | 27.0121 | 98.48 | 80.3 | 30.5068 | 98.56 | 84.78 |
| chr8 | 31.0447 | 99.74 | 88.57 | 25.8972 | 98.62 | 76.71 |
| chr9 | 29.0676 | 99.02 | 82.61 | 27.7328 | 98.25 | 75.31 |
| chr10 | 27.8786 | 99.16 | 82.83 | 27.7149 | 98.6 | 80.43 |
| chr11 | 29.45 | 99.13 | 82.79 | 29.8961 | 98.92 | 82.33 |
| chr12 | 29.4246 | 98.67 | 82.26 | 32.2911 | 98.84 | 83.73 |
| chr13 | 23.7642 | 97.54 | 74.79 | 34.5168 | 98.73 | 86.93 |
| chr14 | 29.7016 | 99.67 | 82.25 | 30.5752 | 98.59 | 85.76 |
| chr15 | 29.6648 | 99.01 | 80.93 | 29.7592 | 99.66 | 84.85 |
| chr16 | 28.2079 | 98.26 | 79.61 | 29.2325 | 98.36 | 83.27 |
| chr17 | 32.6416 | 98.63 | 86.27 | 30.4981 | 98.48 | 82.02 |
| chr18 | 25.0695 | 98.73 | 75.49 | 34.6129 | 98.26 | 85.97 |
| chr19 | 26.0889 | 97.57 | 72.98 | 28.1044 | 95.73 | 72.88 |
| chr20 | 30.171 | 98.08 | 81.9 | 30.3635 | 98.83 | 84.51 |
| chr21 | 23.7753 | 94.16 | 73.36 | 26.8191 | 98.47 | 75.99 |
| chr22 | 30.6012 | 98.26 | 81.74 | 27.5009 | 98.32 | 74.69 |
| chrX | 16.937 | 98.66 | 67.18 | 14.918 | 98.79 | 62.83 |
| chrY | 34.6212 | 100 | 97.14 | 21.3816 | 99.78 | 75.94 |

FIG. 6 shows the length distribution of inserted fragments in sequencing reads, it can be seen from FIG. 6 that the length of inserted fragments is about 160 bp though without screening. FIG. 7 shows the distribution of sequencing depth of each base in the target regions, it can be seen from FIG. 7 that the sequencing depth of most bases (about 75%) was greater than 20×, and the requirement for sequencing cover depth can be met if the amount of sequencing data continues to increase. FIG. 8 shows the frequency of base mismatch at each base position of all mapped reads during the process of reads alignment, according to the principle of sequencing, the quality of sequencing reads will decrease with increased length of reads, and the error rate will increase with increased length of reads. It can also be seen from FIG. 8 that there were considerable amounts of mismatch in reads of the ends, therefore, the sequencing quality of the ends should be taken into consideration during subsequent detection for variation. FIG. 9 shows the coverage of target genes. It can be seen from FIG. 9 that when the depth is greater than 10×, genes of which the coverage is greater than 60% account for 80%, which indicates that the probes can accurately capture genes, and if the amount of sequencing data is larger, all of the related genes can be covered by probes under certain depth. FIG. 10 shows the capture results of histone gene HIST2H3A and the promoter thereof by a probe chip.

So far, the example has described the feasibility of capturing gene promoter region and exon region of epigenome by using a chip, the result of the example can be used for subsequent detection for variation and cytosine methylation. In order to improve accuracy of the detection, it is suggested to increase the amount of sample and sequencing depth.

INDUSTRIAL APPLICABILITY

The method for constructing a high-throughput sequencing library and use thereof, can be conveniently and effectively applied to construct and sequence a high-throughput sequencing library of specified genome regions of a sample, thereby effectively applied to detect and analyze variation and cytosine methylation, and the quality of the obtained library is good and the result of sequencing and analysis is accurate.

Although the description of the embodiment of the present disclosure have been detailed described, it would be appreciated by those skilled in the art. According to all teachings already published, modifications and alternatives can be made with those details, these changes are all within the scope of the present disclosure. The whole scope of the present disclosure is provided by attached claims and any equivalents thereof.

Reference throughout this specification to "an embodiment", "some embodiments", "exemplary embodiment", "an example", "a specific example" or "some examples" means that a particular feature, structure, material or characteristic described in connection with the embodiment or example is included in at least one embodiment or example of the present disclosure. Thus, the appearances of the schematic expressions of the phrases are not necessarily referring to the same embodiment or example of the present disclosure. Furthermore, the described particular features, structures, materials or characteristics may be combined in any suitable manner in one or more embodiments or examples.

What is claimed is:

1. A method for constructing a high-throughput sequencing library, comprising:
fragmenting genomic DNA to obtain DNA fragments;
end-repairing the DNA fragments to obtain end-repaired DNA fragments;
adding a base A to the 3' end of the end-repaired DNA fragments to obtain DNA fragments having cohesive end A;
connecting the DNA fragments having cohesive end A with a methylated adapter to obtain connection products;
carrying out hybrid capture on the connection products by using specific probes to obtain object fragments;
PCR amplifying the object fragments to obtain amplification products; and
separating and purifying the amplification products, wherein the amplification products constitute the high-throughput sequencing library;
wherein the specific probes are specific for known methylation sites,
the specific probes are designed based on using genes in Table I, which are from the human genome and known to have methylation sites, as target sequences,
wherein the specific probes consist of probes together covering at least 200 kb of coding regions or promoter regions spreading from 2200 bp upstream to 500 bp downstream from the transcription start sites of the genes listed in Table I.

2. The method according to claim 1, characterized in that, after carrying out the hybrid capture but before the PCR amplification, the object fragments are treated with bisulfite, such that non-methylated cytosines in the object fragments are converted to uracils.

3. The method according to claim 1, characterized in that, the genomic DNA is genomic DNA from human whole blood.

4. The method according to claim 1, characterized in that, a length of the DNA fragments is in the range of from about 150 to about 300 bp.

5. The method according to claim 1, characterized in that, the methylated adapter comprises a barcode therein.

6. The method according to claim 1, characterized in that, prior to the connection of the DNA fragments having cohesive end A with the methylated adapter, the method further comprises a step of methylating the adapter.

7. The method according to claim 1, characterized in that, the specific probes further comprise probes complementary to a CpG island region, a CGI shore region and an imprinted gene region.

8. The method according to claim 1, characterized in that, prior to the hybrid capture, the method further comprises a step of performing a hybrid blocking on the connection products and the methylated adapter connected to the connection products by using $c_o$t-1 DNA and an adapter block respectively.

9. The method according to claim 1, characterized in that, the step of performing the hybrid capture on the connection products by using the specific probes further comprises a step of capturing the object fragments by using streptavidin magnetic beads.

10. The method according to claim 2, characterized in that, prior to treating the object fragments with bisulfate, the object fragments are mixed with fragmented λ-DNA.

11. A method for identifying methylation information in specified genomic regions of a sample, comprising the following steps of:
   constructing a high-throughput sequencing library of the specified genomic regions of the sample according to the method of claim 1;
   sequencing the high-throughput sequencing library of the specified genomic regions of the sample to obtain sequencing data; and
   analyzing the sequencing data to identify the methylation information in the specified genomic regions of the sample.

12. The method of claim 1, wherein the specific probes include probes covering 200 kb to 24 Mb of the coding regions and promoters of the genes listed in Table I.

\* \* \* \* \*

SEQUENCE LISTING

<160> NUMBER OF SEQ ID NOS: 10

<210> SEQ ID NO 1
<211> LENGTH: 33
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: adapter 1
<220> FEATURE:
<221> NAME/KEY: misc_feature
<222> LOCATION: (1)..(1)
<223> OTHER INFORMATION: phosphorylated
<220> FEATURE:
<221> NAME/KEY: misc_feature
<222> LOCATION: (4)..(4)
<223> OTHER INFORMATION: methylated
<220> FEATURE:
<221> NAME/KEY: misc_feature
<222> LOCATION: (12)..(12)
<223> OTHER INFORMATION: methylated
<220> FEATURE:
<221> NAME/KEY: misc_feature
<222> LOCATION: (14)..(14)
<223> OTHER INFORMATION: methylated
<220> FEATURE:
<221> NAME/KEY: misc_feature
<222> LOCATION: (16)..(16)
<223> OTHER INFORMATION: methylated
<220> FEATURE:
<221> NAME/KEY: misc_feature
<222> LOCATION: (19)..(19)
<223> OTHER INFORMATION: methylated
<220> FEATURE:
<221> NAME/KEY: misc_feature
<222> LOCATION: (24)..(24)
<223> OTHER INFORMATION: methylated
<220> FEATURE:
<221> NAME/KEY: misc_feature
<222> LOCATION: (26)..(27)
<223> OTHER INFORMATION: methylated
<220> FEATURE:
<221> NAME/KEY: misc_feature
<222> LOCATION: (31)..(31)
<223> OTHER INFORMATION: methylated
<220> FEATURE:
<221> NAME/KEY: misc_feature
<222> LOCATION: (33)..(33)
<223> OTHER INFORMATION: methylated

<400> SEQUENCE: 1
gatcggaaga gcacacgtct gaactccagt cac                                33

<210> SEQ ID NO 2
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: adapter 2
<220> FEATURE:
<221> NAME/KEY: misc_feature
<222> LOCATION: (3)..(3)
<223> OTHER INFORMATION: methylated
<220> FEATURE:
<221> NAME/KEY: misc_feature
<222> LOCATION: (5)..(5)
<223> OTHER INFORMATION: methylated
<220> FEATURE:
<221> NAME/KEY: misc_feature

```
<222> LOCATION: (7)..(7)
<223> OTHER INFORMATION: methylated
<220> FEATURE:
<221> NAME/KEY: misc_feature
<222> LOCATION: (11)..(13)
<223> OTHER INFORMATION: methylated
<220> FEATURE:
<221> NAME/KEY: misc_feature
<222> LOCATION: (16)..(16)
<223> OTHER INFORMATION: methylated
<220> FEATURE:
<221> NAME/KEY: misc_feature
<222> LOCATION: (18)..(18)
<223> OTHER INFORMATION: methylated
<220> FEATURE:
<221> NAME/KEY: misc_feature
<222> LOCATION: (21)..(21)
<223> OTHER INFORMATION: methylated
<220> FEATURE:
<221> NAME/KEY: misc_feature
<222> LOCATION: (23)..(23)
<223> OTHER INFORMATION: methylated
<220> FEATURE:
<221> NAME/KEY: misc_feature
<222> LOCATION: (25)..(25)
<223> OTHER INFORMATION: methylated
<220> FEATURE:
<221> NAME/KEY: misc_feature
<222> LOCATION: (28)..(29)
<223> OTHER INFORMATION: methylated
<220> FEATURE:
<221> NAME/KEY: misc_feature
<222> LOCATION: (33)..(33)
<223> OTHER INFORMATION: methylated

<400> SEQUENCE: 2
tacactcttt ccctacacga cgctcttccg atct                                   34

<210> SEQ ID NO 3
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: adapter 1'
<220> FEATURE:
<221> NAME/KEY: misc_feature
<222> LOCATION: (1)..(1)
<223> OTHER INFORMATION: phosphorylated
<220> FEATURE:
<221> NAME/KEY: misc_feature
<222> LOCATION: (1)..(6)
<223> OTHER INFORMATION: n= a, t, c, or g
<220> FEATURE:
<221> NAME/KEY: misc_feature
<222> LOCATION: (11)..(11)
<223> OTHER INFORMATION: methylated
<220> FEATURE:
<221> NAME/KEY: misc_feature
<222> LOCATION: (19)..(19)
<223> OTHER INFORMATION: methylated
<220> FEATURE:
<221> NAME/KEY: misc_feature
<222> LOCATION: (21)..(21)
<223> OTHER INFORMATION: methylated
<220> FEATURE:
<221> NAME/KEY: misc_feature
<222> LOCATION: (23)..(23)
<223> OTHER INFORMATION: methylated
<220> FEATURE:
<221> NAME/KEY: misc_feature
<222> LOCATION: (26)..(26)
<223> OTHER INFORMATION: methylated
<220> FEATURE:
```

-continued

```
<221> NAME/KEY: misc_feature
<222> LOCATION: (31)..(31)
<223> OTHER INFORMATION: methylated
<220> FEATURE:
<221> NAME/KEY: misc_feature
<222> LOCATION: (33)..(34)
<223> OTHER INFORMATION: methylated
<220> FEATURE:
<221> NAME/KEY: misc_feature
<222> LOCATION: (38)..(38)
<223> OTHER INFORMATION: methylated
<220> FEATURE:
<221> NAME/KEY: misc_feature
<222> LOCATION: (40)..(40)
<223> OTHER INFORMATION: methylated

<400> SEQUENCE: 3
nnnnnnagat cggaagagca cacgtctgaa ctccagtcac                    40

<210> SEQ ID NO 4
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(41)
<223> OTHER INFORMATION: adapter 2'
<220> FEATURE:
<221> NAME/KEY: misc_feature
<222> LOCATION: (3)..(3)
<223> OTHER INFORMATION: methylated
<220> FEATURE:
<221> NAME/KEY: misc_feature
<222> LOCATION: (5)..(5)
<223> OTHER INFORMATION: methylated
<220> FEATURE:
<221> NAME/KEY: misc_feature
<222> LOCATION: (7)..(7)
<223> OTHER INFORMATION: methylated
<220> FEATURE:
<221> NAME/KEY: misc_feature
<222> LOCATION: (11)..(13)
<223> OTHER INFORMATION: methylated
<220> FEATURE:
<221> NAME/KEY: misc_feature
<222> LOCATION: (16)..(16)
<223> OTHER INFORMATION: methylated
<220> FEATURE:
<221> NAME/KEY: misc_feature
<222> LOCATION: (18)..(18)
<223> OTHER INFORMATION: methylated
<220> FEATURE:
<221> NAME/KEY: misc_feature
<222> LOCATION: (21)..(21)
<223> OTHER INFORMATION: methylated
<220> FEATURE:
<221> NAME/KEY: misc_feature
<222> LOCATION: (23)..(23)
<223> OTHER INFORMATION: methylated
<220> FEATURE:
<221> NAME/KEY: misc_feature
<222> LOCATION: (25)..(25)
<223> OTHER INFORMATION: methylated
<220> FEATURE:
<221> NAME/KEY: misc_feature
<222> LOCATION: (28)..(29)
<223> OTHER INFORMATION: methylated
<220> FEATURE:
<221> NAME/KEY: misc_feature
<222> LOCATION: (33)..(33)
<223> OTHER INFORMATION: methylated
<220> FEATURE:
<221> NAME/KEY: misc_feature
<222> LOCATION: (35)..(40)
<223> OTHER INFORMATION: n=a, t, g, or c
```

```
<220> FEATURE:
<221> NAME/KEY: misc_feature
<222> LOCATION: (35)..(40)
<223> OTHER INFORMATION: n= a, t, c, or g

<400> SEQUENCE: 4
tacactcttt ccctacacga cgctcttccg atctnnnnnn t                    41

<210> SEQ ID NO 5
<211> LENGTH: 33
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Block 1
<220> FEATURE:
<221> NAME/KEY: misc_feature
<222> LOCATION: (1)..(33)
<223> OTHER INFORMATION: Block1

<400> SEQUENCE: 5
gtgactggag ttcagacgtg tgctcttccg atc                             33

<210> SEQ ID NO 6
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: Block2

<400> SEQUENCE: 6
agatcggaag agcgtcgtgt agggaaagag tgta                            34

<210> SEQ ID NO 7
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: Block1'
<220> FEATURE:
<221> NAME/KEY: misc_feature
<222> LOCATION: (35)..(40)
<223> OTHER INFORMATION: n= a, t, c, or g

<400> SEQUENCE: 7
gtgactggag ttcagacgtg tgctcttccg atctnnnnnn                      40

<210> SEQ ID NO 8
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(41)
<223> OTHER INFORMATION: Block2'
<220> FEATURE:
<221> NAME/KEY: misc_feature
<222> LOCATION: (2)..(7)
```

```
<223> OTHER INFORMATION: n= a, t, c, or g

<400> SEQUENCE: 8
annnnnnaga tcggaagagc gtcgtgtagg gaaagagtgt a                        41

<210> SEQ ID NO 9
<211> LENGTH: 58
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(58)
<223> OTHER INFORMATION: P1 primer

<400> SEQUENCE: 9
aatgatacgg cgaccaccga gatctacact ctttccctac acgacgctct tccgatct     58

<210> SEQ ID NO 10
<211> LENGTH: 64
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(64)
<223> OTHER INFORMATION: tag N
<220> FEATURE:
<221> NAME/KEY: misc_feature
<222> LOCATION: (25)..(30)
<223> OTHER INFORMATION: n=a, t, c. or g

<400> SEQUENCE: 10
caagcagaag acggcatacg agatnnnnnn gtgactggag ttcagacgtg tgctcttccg   60
atct                                                                64
```